(12) United States Patent
Glines et al.

(10) Patent No.: US 6,309,375 B1
(45) Date of Patent: Oct. 30, 2001

(54) DRUG DELIVERY MODULE

(75) Inventors: Robert C. Glines, Cameron Park; Richard D. Phipps; Lauren K. Lundquist, both of Morgan Hill; Daniel S. Brown, Los Gatos, all of CA (US)

(73) Assignee: MicroHeart, Inc., Sunnyvale, CA (US)

( * ) Notice: Subject to any disclaimer, the term of this patent is extended or adjusted under 35 U.S.C. 154(b) by 0 days.

(21) Appl. No.: 09/314,459

(22) Filed: May 18, 1999

(Under 37 CFR 1.47)

Related U.S. Application Data

(63) Continuation-in-part of application No. 09/080,175, filed on May 16, 1998, now Pat. No. 6,183,444.

(51) Int. Cl.⁷ ..................................................... A61M 5/06
(52) U.S. Cl. .......................................... 604/187; 604/207
(58) Field of Search ................................... 604/207, 187, 604/131, 134, 135, 136, 138, 137, 144, 151, 152, 181, 191, 197, 208, 209, 210, 211, 218, 232, 234, 240; 606/104, 114

(56) References Cited

U.S. PATENT DOCUMENTS

| | | | |
|---|---|---|---|
| 2,491,978 | * | 12/1949 | Helfman et al. . |
| 4,576,591 | * | 3/1986 | Kaye et al. . |
| 4,861,339 | * | 8/1989 | Jonichkeit . |
| 5,034,003 | * | 7/1991 | Denance . |
| 5,106,370 | * | 4/1992 | Stewart . |
| 5,228,883 | * | 7/1993 | Blakely et al. . |
| 5,322,511 | * | 6/1994 | Armbruster et al. . |
| 5,395,312 | * | 3/1995 | Desai . |
| 5,569,160 | * | 10/1996 | Sauer et al. . |
| 5,865,811 | * | 2/1999 | Doying, Sr. et al. . |
| 6,183,444 | * | 2/2001 | Glines et al. . |

* cited by examiner

Primary Examiner—Richard K. Seidel
Assistant Examiner—Kevin C. Sirmons
(74) Attorney, Agent, or Firm—Peter J. Dehlinger; Gregory L. Heinkel; Perkins Coie LLP

(57) ABSTRACT

A modular drug delivery system for use by cardiothoracic surgeons and interventional cardiologists for delivery of molecular and cellular therapies that target genes, molecules and peptides. The regulated drug delivery devices comprise a modular mechanically actuated drug delivery module (DDM) that can be attached to either a surgical viewing endoscope hand-piece or specialized catheter for interventional procedures. The DDM provides metering of drugs to treatment sites and allows for quick interchangeability with other component parts such as a viewing scope end portion for MIS or other surgical procedures or a flexible catheter shaft for percutaneous procedures.

12 Claims, 24 Drawing Sheets

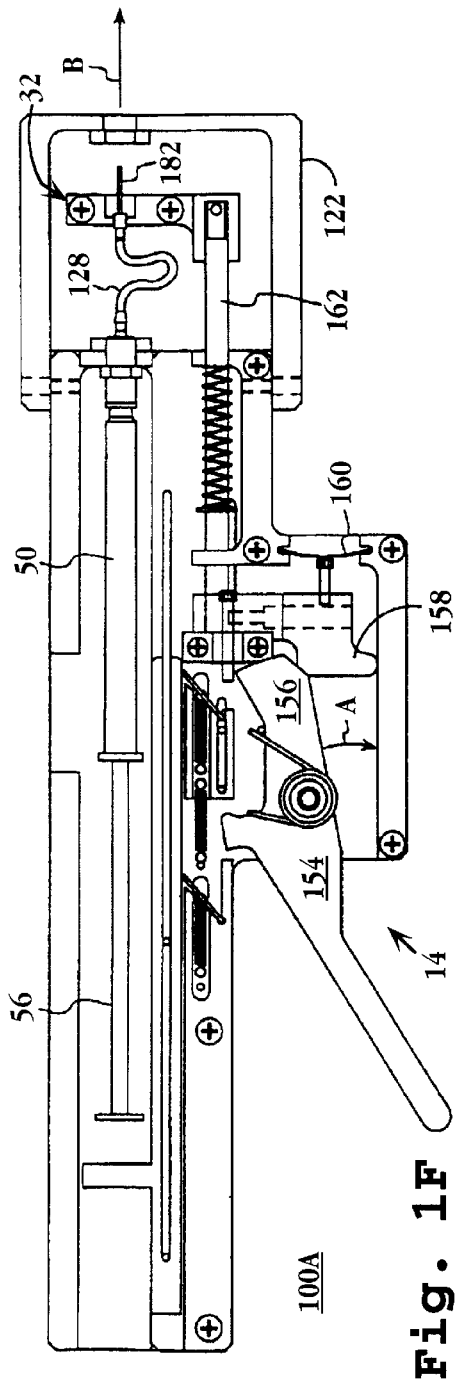

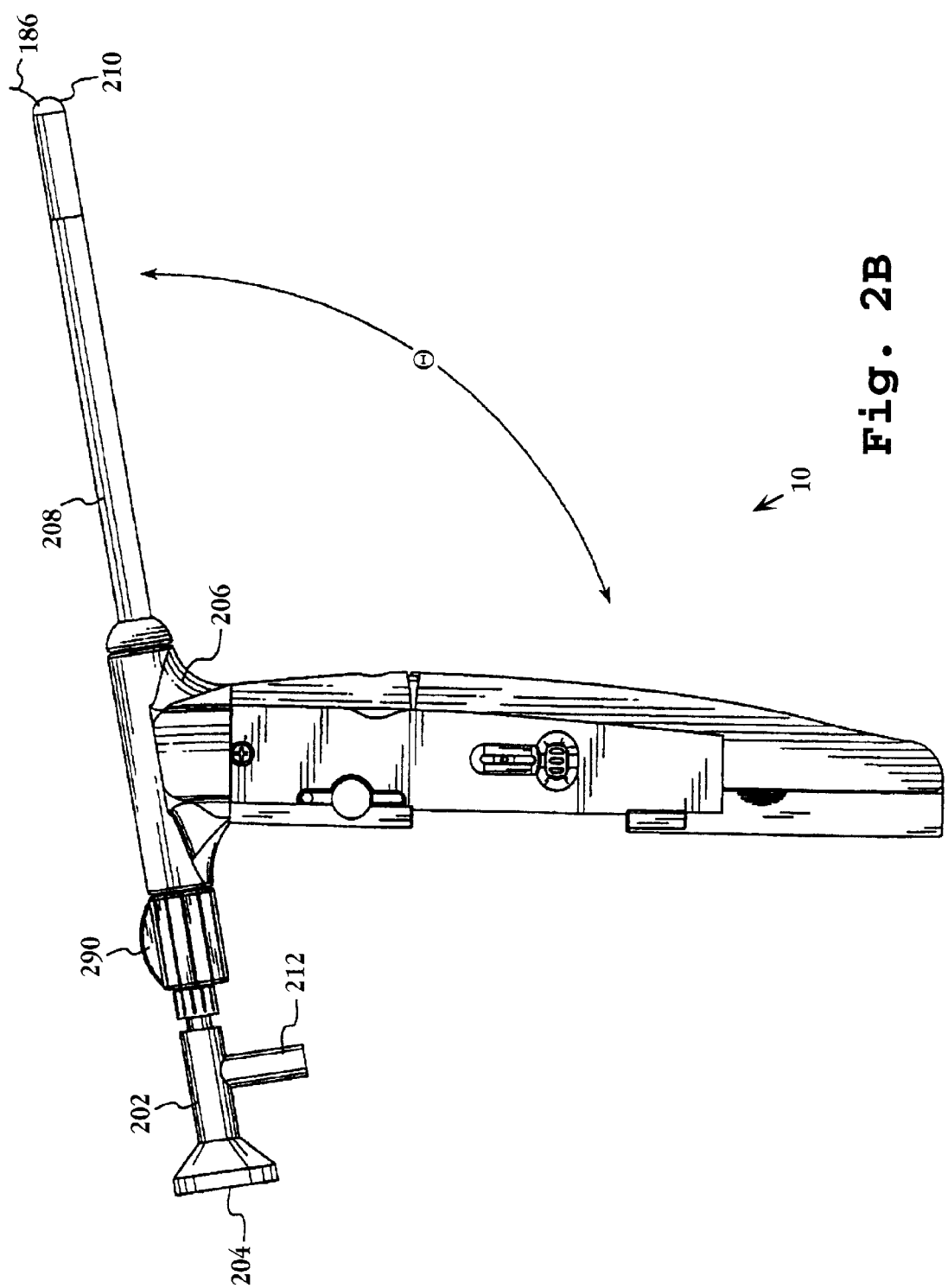

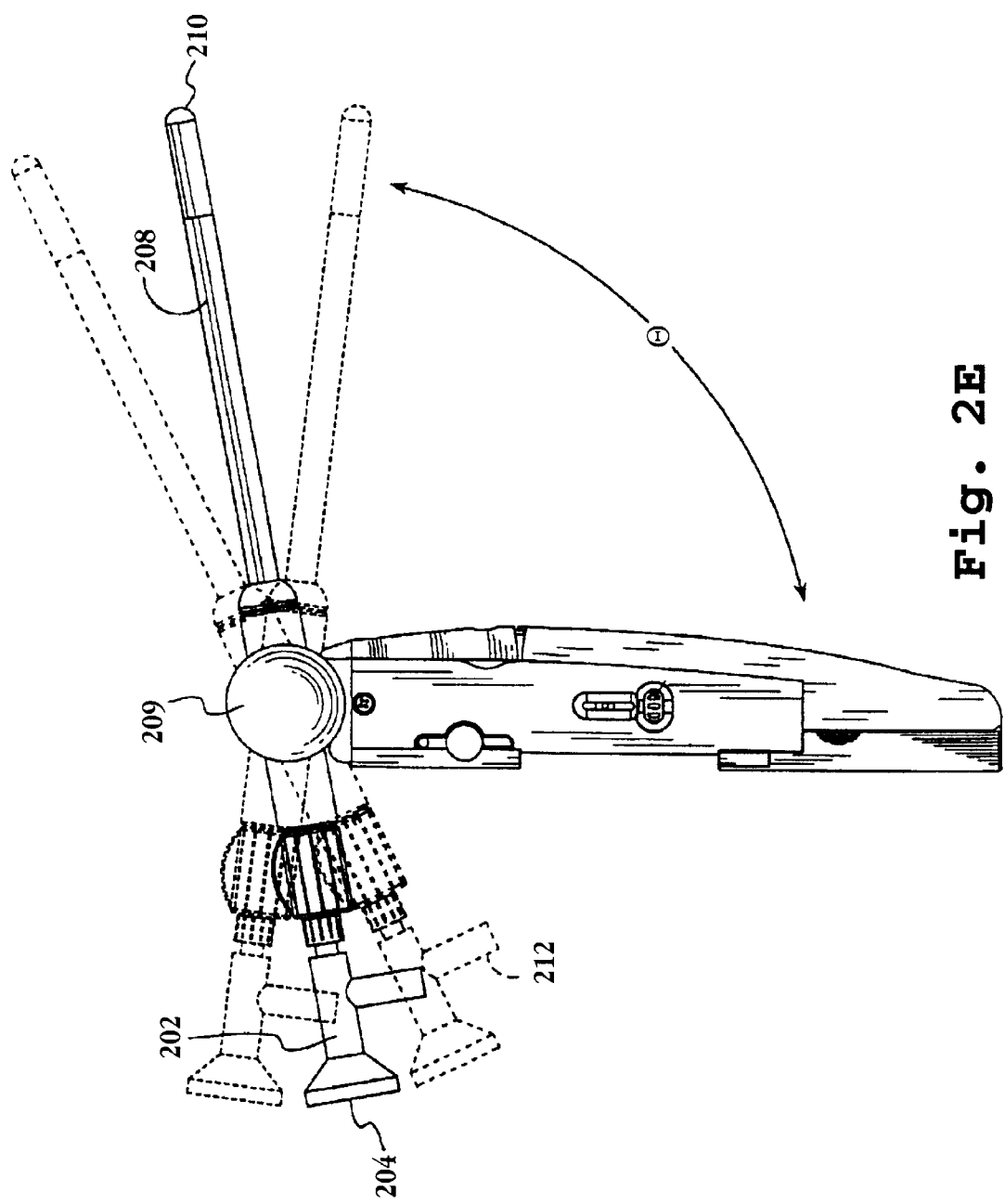

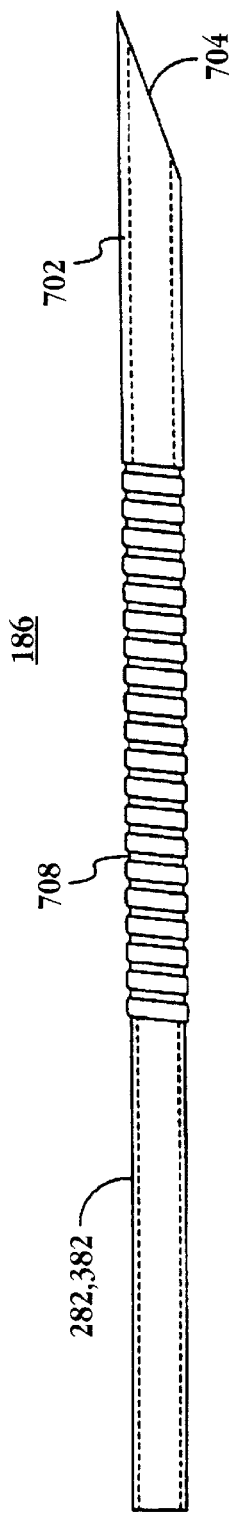
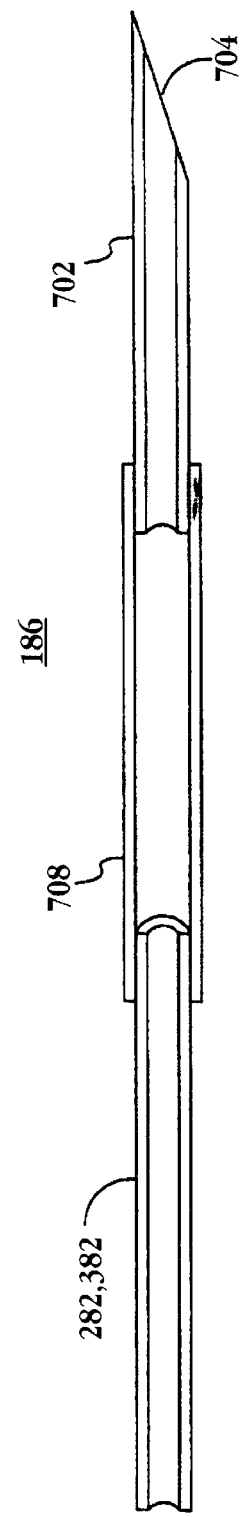
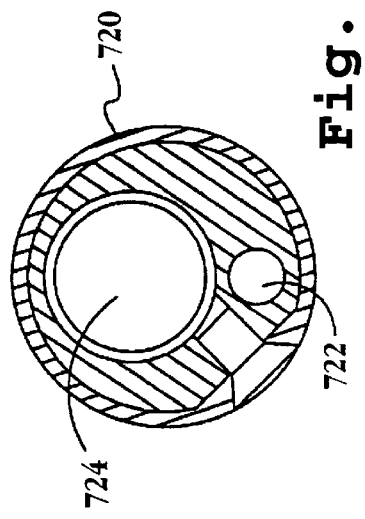

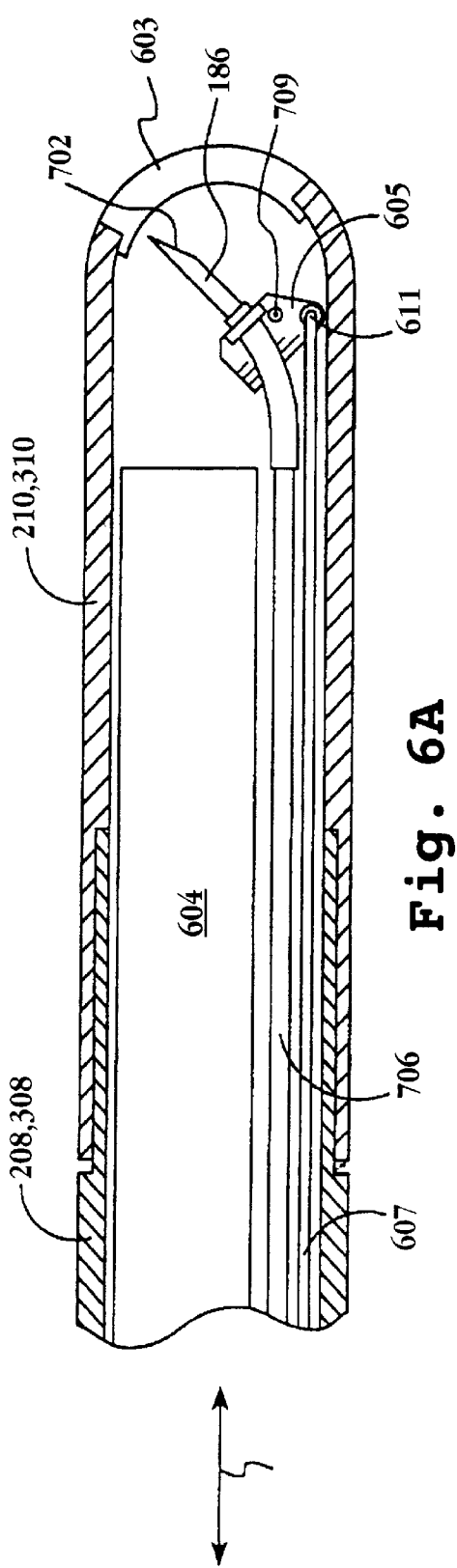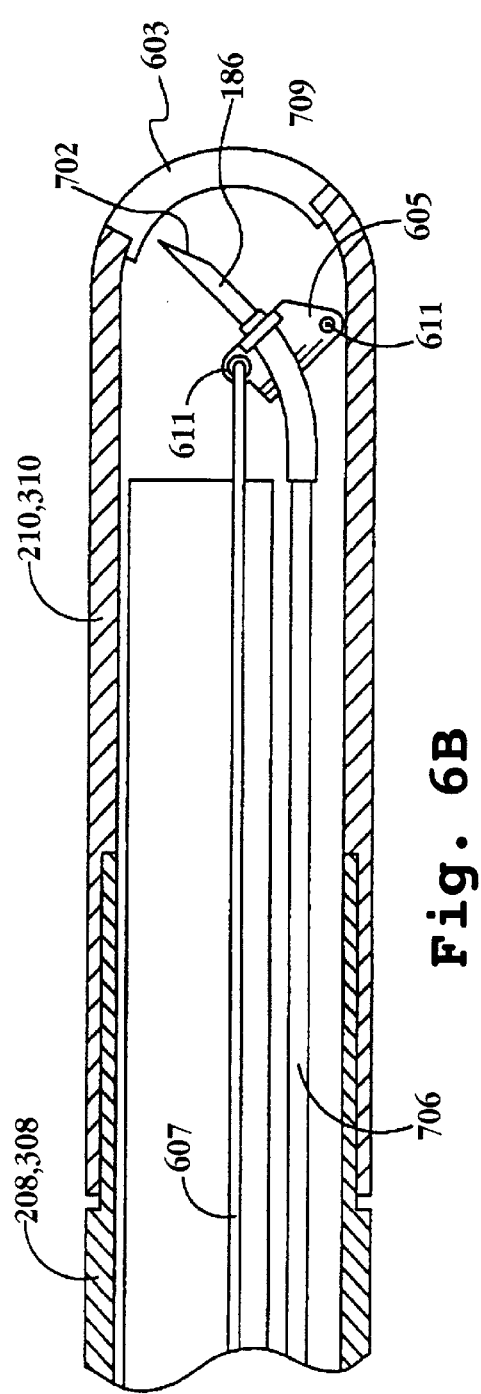
Fig. 6A
Fig. 6B

DRUG DELIVERY MODULE

This application is a continuation-in-part of U.S. application Ser. No. 09/080,175, now U.S. Pat. No. 6,183,444 B1 filed May 16, 1998, which is incorporated herein by reference in its entirety.

FIELD OF THE INVENTION

The present invention is directed to a device and method for delivering selected therapeutic and/or diagnostic agents to target sites in selected body tissues or organs, such as the heart. More particularly, the invention provides a module, or device, that can be used with a medical appliance, such as a catheter or endoscope-type assembly, for delivering such agents by injection through a needle.

BACKGROUND OF THE INVENTION

The human heart is a muscular dual pump that beats continuously throughout life sending blood to the lungs and the rest of the body. The interior of the heart consists of four distinct chambers. The septum, a thick central muscular wall, divides the cavity into right and left halves. On the right side, the upper half is known as the right atrium. Deoxygenated blood from the rest of the body arrives in the right atrium via the vena cava, the blood is pumped across a one-way valve known as the tricuspid valve into the lower portion known as the right ventricle. From there the blood circulates to the lungs through the pulmonary valve via the pulmonary artery where it is oxygenated by circulation through the alveoli of the lungs (not shown). The blood returns via the pulmonary veins to the left atrium and flows through a second valve, the mitral valve into the left ventricle where it is pumped via the aorta to the rest of the body.

Much of the heart consists of a special type of muscle called myocardium. The myocardium requires a constant supply of oxygen and nutrients to allow it to contract and pump blood throughout the vasculature. The inner surfaces of the chambers of the heart are lined with a smooth membrane, the endocardium, and the entire heart is enclosed in a tough, membranous bag known as the pericardial sac.

The pumping action of the heart has three main phases for each heart beat. Diastole is the resting phase during which the heart fills with blood: while deoxygenated blood is entering the right atrium, oxygenated blood is returned from the lungs to the left atrium. During atrial systole, the two atria contract simultaneously, squeezing the blood into the lower ventricles. Finally, during ventricular systole the ventricles contract to pump the deoxygenated blood into the pulmonary arteries and the oxygenated blood into the main aorta. When the heart is empty, diastole begins again. The electrical impulses which stimulate the heart to contract in this manner emanate from the heart's own pacemaker, the sinoatrial node. The heart rate is under the external control of the body's *autonomic nervous system.*

Though the heart supplies blood to all other parts of the body, the heart itself has relatively little communication with the oxygenated blood supply. Thus, the two coronary arteries, the left coronary artery and the right coronary artery, arise from the aorta and encircle the heart muscle on either side "like a crown" to supply the heart itself with blood.

Heart disorders are a common cause of death in developed countries. They also impair the quality of life of millions of people and restrict activity by causing pain, breathlessness, fatigue, fainting spells and anxiety. The major cause of heart disease in developed countries is impaired blood supply. The coronary arteries become narrowed due to Atherosclerosis and part of the heart muscle is deprived of oxygen and other nutrients. The resulting ischemia or blockage can lead to angina pectoris, a pain in the chest, arms or jaw due to lack of oxygen to the heart's myocardium, infarction or tissue necrosis in myocardial tissue.

Techniques to supplement the flow of oxygenated blood directly from the left ventricle into the myocardial tissue have included needle acupuncture to create transmural channels (see below) and implantation of T-shaped tubes into the myocardium. Efforts to graft the omentum, parietal pericardium, or mediastinal fat to the surface of the heart had limited success. Others attempted to restore arterial flow by implanting the left internal mammary artery into the myocardium.

Modernly, coronary artery blockage can be relieved in a number of ways. Drug therapy, including nitrates, beta-blockers, and peripheral vasodilator drugs (to dilate the arteries) or thrombolytic drugs (to dissolve clots) can be very effective. If drug treatment fails, transluminal angioplasty is often indicated - the narrowed part of the artery, clogged with atherosclerotic plaque or other deposits, can be stretched apart by passing a balloon to the site and gently inflating it a certain degree. In the event drug therapy is ineffective or angioplasty is too risky (introduction of a balloon in an occluded artery can cause portions of the atherosclerotic material to become dislodged which may cause a total blockage at a point downstream of the subject occlusion, thereby requiring emergency procedures), the procedure known as coronary artery bypass grafting (CABG) is the most common and successful major heart operation performed, with over 500,000 procedures done annually in America alone. A length of vein is removed from another part of the body. The section of vein is first sewn to the aorta and then sewn onto a coronary artery at a place such that oxygenated blood can flow directly into the heart. CABG typically is performed in an open chest surgical procedure, although recent advances suggest minimally invasive surgery (MIS) techniques may also be used.

Another method of improving myocardial blood supply is called transmyocardial revascularization (TMR), the creation of channels from the epicardial to the endocardial portions of the heart. Initially, the procedure used needles to perform "myocardial acupuncture," and has been experimented with at least as early as the 1930s and used clinically since the 1960s, see Deckelbaum. L. I., Cardiovascular Applications of Laser Technology, *Lasers in Surgery and Medicine* 15:315–341 (1994). The technique was thought to relieve ischemia by allowing blood to pass from the ventricle through the channels either directly into other vessels perforated by the channels or into myocardial sinusoids which connect to the myocardial microcirculation. This procedure has been likened to transforming the human heart into one resembling that of a reptile. In the reptile heart, perfusion occurs via communicating channels between the left ventricle and the coronary arteries. Frazier, O. H., Myocardial Revascularization with Laser—Preliminary Findings, *Circulation*, 1995; 92 [suppl II:II -58-II-65]. There is evidence of these communicating channels in the developing human embryo. In the human heart, myocardial microanatomy involves the presence of myocardial sinusoids. These sinusoidal communications vary in size and structure, but represent a network of direct arterial-luminal, arterial-arterial, arterial-venous, and venous-luminal connections. The needle technique was not continued because the channels did not remain open, replaced by the use of laser energy to accomplish TMR.

Drug therapies with angiogenic growth factors may expedite and/or augment collateral artery development. To accomplish these needs, drug transfer devices for delivering precise amounts of these drugs can enhance this healing process. Surgeons who deal with minimally invasive surgical techniques, and interventional cardiologists who deal with percutaneous approaches, need devices for drug delivery procedures. The drugs used in modern medical technology are often quite expensive, potentially mixing and/or handling sensitive, and it is a new challenge to make these drugs or other compounds readily available for precise, predetermined delivery during these advanced or other procedures.

A great deal of published scientific information is currently available on the internet. One company, Annual Reviews is located at http://www.annurev.org. A list of genetically engineered and/or naturally occurring drugs or other agents having pharmacological activity or other utility is located at http://www.annurev.org/sup/im/im15/im15b.htm. Additional scientific information is available at http://darwin.bio.uci.edu/~cchughes/index.html.

Prior drug injection devices include non-articulating, viewing devices. U.S. Pat. No. 5,685,853 issued Nov. 11, 1997 to Bonnet teaches of a partially rigid endoscope to which is attached an injection or aspiration cannula that is axially adjustable along the shaft of the endoscope.

Prior devices also include viewing devices for cardiac interventional procedures. U.S. Pat. Nos. 4,784,133 issued Nov. 15, 1988 and 4,976,710 issued Dec. 11, 1990, both to Mackin, both teach of a flexible angioscope/bronchoscope device with an inflatable balloon structure for viewing intravasculature structures. These flexible catheter devices include a ported working channel for introduction of a working device and positioning of the working device at the viewing/treatment distal end.

U.S. Pat. No. 5,261,889 issued Nov. 16, 1993 to Laine et al. teaches of an injection therapy catheter that is insertable through a working channel in an endoscope for delivering fluid agents through a hollow needle at the distal end of the catheter. The patent does not, however, teach of a modular drug delivery device which can be adapted for either surgical, MIS or catheter/percutaneous procedures, in which controllable drug delivery can be achieved.

U.S. Pat. No. 4,350,148 issued Sep. 21, 1982 to Sivak, Jr. et al. also teaches of a drug injector device, in this case for treating esophageal varices. A flexible shafted endoscope has a conduit with distal ended needle is inserted in the endoscope's biopsy channel for effectuating the treatment.

Drug regulating injection mechanisms such as those shown in U.S. Pat. Nos. 4,475,905 issued Oct. 9, 1984 to Himmelstrup, U.S. Pat. no.5,468,233 issued Nov. 21, 1995 to Schraga and 5,697,916 issued Dec. 16, 1997 also to Schraga which teach of devices for regulating drug delivery using a syringe with mechanisms for controlling plunger operation for metered dosages.

U.S. Pat. Nos. 4,702,260 issued Oct. 27, 1987 and U.S. Pat. Nos. 4,766,906 issued Aug. 30, 1988, both to Wang, teach bronchoscopic needle assemblies. The needle assemblies are especially adapted for safe and efficacious collection of biopsy samples.

U.S. Pat. No. 5,554,114 issued Sep. 10, 1996 to Wallace et al. teaches an infusion device with preformed shape. An infusion guidewire or catheter is used for introduction of the device through a selected path in a patient's vascular system. An elongated tubular diffusion body lies at the distal end of an elongated tube, the diffusion portion having a plurality of infusion ports through which blood, drug, diagnostic agent or other material can be delivered to the particular site in the vascular system. No metering system or other mechanism is disclosed, however, whereby a predetermined dosage rate through the diffusion device can be achieved.

U.S. Pat. No. 5,685,853 issued Nov. 11, 1997 to Bonnet teaches an injection device by means of an injection caniula axially adjustable along an endoscope shaft. The injection cannula and guide tube are axially adjustable relative to the endoscope shaft by means of a handle which can be operated with one hand.

U.S. Pat. No. 5,464,394 issued Nov. 7, 1995 to Miller et al. teaches a multilumen percutaneous angioscopy catheter which allows simultaneous irrigation and passage of an angioscope therethrough.

U.S. Pat. No. 5,409,453 issued Apr. 25, 1995 to Lundquist et al. teaches a steerable medical probe with stylets. The device is designed for reducing the mass of a body part, such as for biopsy sampling or for removing prostatic tissue in the case of BPH. The torquable catheter has a control end and a probe end, the probe end having a stylet guide means with a flexible tip and a tip directing means extending from the control end to the flexible tip for changing the orientation of the central axis of the stylet guide means for directing a flexible stylet outward through the stylet port and through intervening tissue to targeted tissues.

U.S. Pat. No. 5,571,151 issued Nov. 5, 1996 to Gregory teaches a method for contemporaneous application of laser energy and localized pharmacologic therapy. The method comprises preparing a solution of a pharmacologic agent, inserting the catheter into the lumen, directing the catheter to the site, transmitting visible light to the site, flowing the light transmissive liquid through the catheter, viewing the site, transmitting laser energy through the liquid filled catheter to treat the site, and introducing a flow of the pharmacologic agent in solution into the catheter for contemporaneous discharge at the distal end into the lumen adjacent the site.

International Publication No. WO 92/10142 published Jun. 25, 1992 by Pfizer Hospital Products Group and Makower teaches a device and method for interstitial laser energy delivery. A catheter with moveable needle system places one or more fiber optic elements and thermo-measuring devices through a body passageway wall and into the bulk of an adjacent organ. The catheter is positioned adjacent to the organ and the needles are extended to mechanically puncture the wall and move into the organ with the fiber optic elements. The needle may be withdrawn into the catheter before delivery of laser energy or remain in the organ to serve as an aspiration-irrigation vehicle. Lumens provided within the catheter for carrying the hollow needles may likewise be used for aspiration or irrigation of the passageway. The devices may also be used with a dilatation balloon, etc.

Thus, there is a need to provide a modular, adaptable, universally utilitarian drug delivery module which provides remote needle advance and metered drug delivery. There is also a need for a hand-held driig delivery device with regard to the described drug delivery module.

There is a need for a device for performing drug delivery from either one or inmore minimally invasive penetrations, such as in a patient's chest, and/or percutaneously, such as through the vasculature, and while viewing the procedure for efficacious delivery. Moreover, there is a need for quick interchangeability or other adaptability for regulated druo delivery, such as in a modular, adaptable system.

It would also be desirable to provide a drug delivery device which enables rapid deployment of a drug delivery needle for rapid delivery of the drug at a distal point in a patient. Reducing the overall time of intervention is often desirable, and the faster a needle can be injected, drug dispensed and the needle retracted, the less chance of causing undesirable effects.

SUMMARY OF THE INVENTION

One aspect of the present invention provides a module, or device, for delivering selected therapeutic and/or diagnostic agents to target sites in selected body tissues or organs, such as the heart, by injection through a needle.

In one general embodiment, the drug-delivery module, or device, of the present invention includes a housing with an actuator mounted thereon for movement between open and closed positions, and a carriage assembly mounted therein for movement between retracted and extended positions. The carriage assembly includes a linkage connectable to a needle for needle movement with the carriage assembly between retracted and extended needle positions. The linkage can be, for example, a conduit adapted to be connected in fluid communication with the needle. One or more fluid reservoirs are adapted for fluid connection to the needle. Advancing means operatively connect the actuator to the carriage assembly, to advance the assembly toward its extended position when the actuator is moved from its open position, toward its closed position. Compressing means operatively connect the actuator to the reservoir for compressing the reservoir when the actuator is moved from its open position, toward its closed position.

In one embodiment of the device, the advancing means is effective to advance the carriage assembly toward its extended position when the actuator is moved from its open position, toward a position intermediate its open and closed positions; and the compressing means is effective to compress the reservoir when the actuator is moved from a position intermediate its open and closed positions toward its closed position.

The actuator can include, for example, a manually-operable handle operable between such open and closed positions, and a pivoting member mounted in the housing for pivoting movement in forward and reverse directions, as the actuator is moved toward and away from its closed position, respectively.

In one embodiment, the advancing means includes a sliding surface contact between the pivoting member and the carriage assembly. In another embodiment, the advancing means includes a two-condition spring interposed between the pivoting member and carriage assembly, effective to flip from one condition to another, when a selected spring tension is reached, to move the carriage assembly toward its extended position.

The reservoir can be, for example, a syringe barrel having an outlet in fluid communication with the conduit. The compressing means can include, for example, a plunger movable within the syringe barrel toward the outlet, to expel fluid from the reservoir. In one embodiment, wherein the actuator includes a manually operable handle operable between such open and closed positions, and a pivoting member mounted in the housing for pivoting movement in forward and reverse directions, as the actuator is moved toward and away from its closed position, respectively; the compressing means ftirther includes (a) a sliding bar operatively engageable at one bar end with the plunger, (b) a reciprocating bar connected at one bar end to the pivoting member, for movement in forward and reverse directions as the pivoting member is pivoted in forward and reverse directions, respectively, and (c) a releasable locking mechanism operably coupling the sliding bar and the reciprocating bar, such that successive actuations of the actuator are effective to advance the sliding bar incrementally in a forward direction effective to expel a defined and incremental quantity of fluid from the reservoir with each such actuation. The releasable locking mechanism can include, for example, first and second pivot plates, with the first plate being operatively connected to the reciprocating bar, and adapted to engage or release the sliding bar, as the reciprocating bar is advanced in a forward or reverse direction, respectively; and the second plate being pivotally mounted adjacent the sliding bar, and adapted to release or engage the sliding bar as the reciprocating bar is advanced in a forward or reverse direction, respectively. The advancing means can include, for example, a sliding surface contact between the pivoting member and the carriage assembly, with the advancing means being effective to advance the carriage assembly toward its extended position when the actuator is moved from its open position, toward a position intermediate its open and closed positions, and the compressing means being effective to compress the reservoir when the actuator is moved from a position intermediate its open and closed positions toward its closed position.

One embodiment of the device is particularly well suited for use with an appliance adapted to access a body target site. An exemplary appliance, in this regard, includes (i) an elongate hollow body probe with proximal and distal ends and an inner lumen extending therebetween, (ii) an extension member contained within the lumen and extending substantially the length of the probe from a proximal to a distal probe end, and (iii) a needle carried at the distal end of the extension member. The device, in this embodiment, is adapted to be detachably connected to the proximal end of the body probe, with the linkage being operatively connected to the extension member, and the reservoir being in fluid communication with the needle, such that (i) movement of the carriage assembly from its retracted to its extended position is transmitted to the extension member, causing the needle at the distal end of the appliance to move from a retracted to an injection position, and (ii) fluid contained in the reservoir and forced from the reservoir is effective to force a drug solution in the appliance through the needle.

The linkage can be, for example, a conduit; and the extension can be a hollow tube adapted to be connected in fluid communication with the conduit, to transmit fluid pressure from the reservoir to the needle. In one embodiment, the drug solution is contained in the distal end of the tube.

In another embodiment, the drug solution is contained in a drug container adjacent the distal end of the appliance; and fluid pressure transmitted from the reservoir through the tube is effective to drive drug solution from the container through the needle.

The extension can be, for example, a wire member operatively connected to the linkage. Additionally, a fluid-carrying tube can be provided in the device for transmitting fluid pressure from the reservoir to the needle. In one embodiment, the drug solution is contained in the distal end of the tube.

In another embodiment, the drug solution is contained in a drug container adjacent the distal end of the appliance, and fluid pressure transmitted from the reservoir through the tube is effective to drive drug solution from the container through the needle.

The appliance can be, for example, a catheter assembly, and the probe a hollow catheter sleeve. Or, the applicance can be an endoscope assembly, and the probe a hollow tube. In one embodiment of the latter, the distal end of the probe has an endoscopic lens, and the needle is moved from its retracted to extended positions through the lens.

Another aspect of the present invention provides an apparatus for delivery of a drug solution to a target site within a subject by needle injection.

One general embodiment of the apparatus includes: (a) a delivery device having (i) a housing, (ii) a fluid reservoir, (iii) a carriage assembly mounted in the housing for movement between retracted and extended conditions, and (iv) an actuator assembly operatively connected to the carriage and the reservoir to cause movement of the carriage from its retracted toward its extended position and flow of fluid from the reservoir, as the actuator is moved from open to closed positions; and (b) an appliance maneuverable within a subject to such target site, with the appliance having (i) an elongate hollow body probe with proximal and distal ends, and an inner lumen extending therebetween, (ii) an extension member extending substantially the length of the probe from a proximal to a distal probe end, and (iii) a needle carried at the distal end of the extension member. The extension member, in this general embodiment, is operatively connected to the carriage, and the needle is in fluid communication with the reservoir, such that (i) movement of the carriage assembly from its retracted to its extended position is transmitted to the extension member, causing the needle at the distal end of the appliance to move from a retracted to an injection position into the target tissue, and (ii) fluid contained in the reservoir and forced from the reservoir is effective to force a drug solution contained in the appliance through the needle for delivery into the target site.

According to one embodiment, the actuator assembly includes (i) an actuator mounted on the housing for movement between open and closed positions, (ii) advancing means operatively connecting the actuator to the carriage assembly, to advance the carriage assembly toward its extended position when the actuator is moved away from its open position, toward its closed position, and (iii) compressing means operatively connecting the actuator to the reservoir for compressing the reservoir when the actuator is moved from its open position, toward its closed condition.

In one embodiment, the advancing means is effective to advance the carriage assembly toward its extended position when the actuator is moved from its open position, toward a position intermediate its open and closed positions; and the compressing means is effective to compress the reservoir when the actuator is moved from a position intermediate its open and closed positions toward its closed position.

One embodiment provides the reservoir contained in the housing. More particularly, in this embodiment, the reservoir is a syringe barrel having an outlet in fluid communication with the needle. Further in this embodiment, the compressing means includes a plunger movable within the barrel toward the outlet, to expel fluid from the reservoir.

In an exemplary arrangement, the actuator includes a handle operable between such open and closed positions, and a pivoting member mounted in the housing for pivoting movement in forward and reverse directions, as the actuator is from toward and away from its closed position, respectively. The compressing means, in this exemplary arrangement, further includes (a) a sliding bar operatively engageable at one bar end with the plunger, (b) a reciprocating bar connected at one bar end to the pivoting member, for movement in forward and reverse directions as the pivoting member is pivoted in forward and reverse directions, respectively, and (c) a releasable locking mechanism operably coupling the sliding bar and reciprocating bar, such that successive actuations of the actuator are effective to advance the sliding bar incrementally in a forward direction effective to expel a defined and incremental quantity of fluid from the reservoir with each such actuation. The locking mechanism can include, for example, first and second pivot plates, with the first plate being operatively connected to the reciprocating bar, and adapted to engage or release the sliding bar, as the reciprocating bar is advanced in a forward or reverse direction, respectively; and with the second plate being pivotally mounted adjacent the sliding bar, and adapted to release or engage the sliding bar as the reciprocating bar is advanced in a forward or reverse direction, respectively.

In one embodiment, wherein the actuator includes a manually operable handle operable between such open and closed positions, and a pivoting member mounted in the housing for pivoting movement in forward and reverse directions, as the actuator is moved toward and away from its closed position, respectively; the advancing means is (i) a sliding surface contact between the pivoting member and the carriage assembly, or (ii) a two-condition spring interposed between the pivoting member and carriage assembly, effective to flip from one condition to another, when a selected spring tension is reached, to move the carriage toward its extended position.

One embodiment of the carriage assembly includes a carriage and a conduit attached thereto, and in fluid communication with the reservoir. The extension can be, for example, a hollow tube in fluid communication with the conduit, for transmitting fluid pressure from the reservoir to the needle. In one such embodiment, a drug solution is contained in the distal end of the tube.

In another embodiment, a drug solution is contained in a drug container adjacent the distal end of the appliance, and fluid pressure transmitted from the reservoir through the tube is effective to drive drug solution from the container through the needle.

Another embodiment of the carriage assembly includes a carriage and a linkage attached thereto. In this embodiment, the extension is a wire member operatively connected to the linkage, and the device fuither includes a fluid-carrying tube for transmitting fluid pressure from the reservoir to the needle.

The appliance can be, for example, a catheter assembly, with the probe being a hollow catheter sleeve. Or, the appliance can be an endoscope assembly, with the probe being a hollow tube.

It will be appreciated that the present invention offers many advantages. For example, one advantage of the present invention is to provide a more efficient, systematic approach to drug delivery.

Another advantage of the present invention is to provide a drug delivery module (DDM) in which a single step, manual activation effects drug conduit/piercing needle advance, subsequent drug delivery therethrough and, optionally, needle retraction, the sequence of operations to be performed efficiently and effectively.

Another advantage of the present invention is to provide a drug delivery device adapted for both surgical/MIS procedures and catheter/percutaneous procedures.

Another advantage of the present invention is to provide a device for regulated drug delivery through at least one minimally invasively formed penetration of a patient's chest.

Another advantage of the present invention is to provide a modular drug delivery device adapted for both surgical/MIS procedures and catheter/percutaneous procedures.

Another advantage of the present invention is to provide a drug delivery device adapted for delivery of small, precisely measured volumes of expensive compounds or materials.

Another advantage of the present invention is to provide a drtig delivery device having indexed adjustability or infinitely variable adjustability of dosage rate, volume, etc., such as over a predetermined range.

Another advantage of the present invention is to provide a drug delivery device adapted for delivery of mixtures of one or more drugs or agents, such as in one or more phases or having varying or similar degrees of miscibility therebetween.

Another advantage of the present invention is to provide a drug delivery device adapted for delivery of mixture sensitive materials.

Another advantage of the present invention is to provide a drug delivery device adapted for delivery and handling of sensitive materials.

Another advantage of the present invention is to provide a device for minimally invasive surgery (MIS) which is sufficiently rigid to support surrounding tissue, and which allows drug delivery at various angles to the central axis of the device relative to a target tissue location.

Another advantage of the present invention is to provide a drug delivery device which enables rapid deployment of a drug delivery needle for rapid delivery of the drug at a distal point in a patient.

In one general embodiment, the present invention is a drug delivery module for performing both interventional and minimally invasive surgical (MIS) drug delivery procedures on or in the human body or organs therein, such as in the heart. The system utilizes a modular, metering or otherwise controllable drug delivery assembly, herein referred to as a drug delivery module (DDM) or device, that includes a hypodermic needle for introducing druIgs at target tissue sites through surgical or minimally invasive penetrations in a patient's chest. One preferred use of the device is for delivering drugs or other agents to a heart after undergoing myocardial revascularization or coronary artery bypass grafting (CABG) or other treatment.

One drug delivery embodiment is essentially a rigid endoscope. Various designs of the drug delivery conduit channel from which the hypodermic needle can egress from the viewing surgical scope are possible. One embodiment includes, for example, a closed ended introducer member with a preferably convex shaped tip that can be pushed against the heart and allows viewing of selected or target tissue, such as a beating heart, while delivering drug. The introducer also stops bleeding by applied pressure, and can perform multiple operative procedures from the same MIS penetration through the chest wall or other body part. The device of this embodiment can further include a pistol-grip type hand-piece which includes regulating drug delivery mechanisms for required dosages.

Several subassembly mechanisms of the drug delivery module can be encompassed in a modular hand grip housing, in a manner permitting interchangeability and use of other required drugs and or instruments in the procedure. The introducer member allows for quick disconnect and interchangeability for operating on both lateral anterior and posterior sides of the heart from a single penetration in a patient's chest. The introducer member is, optionally, a reusable member.

Another embodiment of the DDM is an articulating catheter device which uses a catheter with an atraumatic distal end for guiding the distal end of the catheter through the vasculature without causing damage at any undesired point therein, with an actuable hypodermic drug delivery needle. The atraumatic distal end has a sheath, retractable piercing portion or other safety means. This embodiment includes a similar regulating drug delivery module (DDM) handle member as in the previous embodiment.

A method of the invention includes introducing a drug delivery device through at least a first minimally invasive penetration. A hypodermic drug delivery needle contained within a working channel of the drug delivery device is deployed at the target tissue. Regulated drug delivery is then performed into selected tissue.

A transluminal or percutaneous method of the present invention includes the steps of introducing a hypodermic drug delivery needle through a flexible catheter and deploying same at the target tissue. Regulated drug delivery is then performed into selected tissue.

These and other objects of the invention are achieved in a drug delivery device that is atraumatic to surrounding tissue, minimizes bleeding, and reduces any adverse effect of target tissue movement.

Numerous other advantages and features of the present invention will become readily apparent from the following detailed description of the invention and the embodiments thereof, from the claims and from the accompanying drawings.

BRIEF DESCRIPTION OF THE DRAWINGS

The structure and manner of operation of the invention, together with the further objects and advantages thereof, may best be understood by reference to the following description taken in conjunction with the accompanying drawings, in which:

FIG. 1F is a representative view of an alternative, over-center-type drug delivery device mechanism to fire a piercing needle of the DDM of the present invention.

FIG. 1G is a representative view of another embodiment of a spring loaded-type drug delivery of the DDM of the present invention.

FIG. 2B is a representative side view of a modular or unitary endoscope-type drug delivery device of the present invention.

FIG. 2E is an isometric view of an articulating endoscope-type drug delivery device of the present invention.

FIG. 5A is a representative side view of a flexible piercing needle of the drug delivery devices of the present invention.

FIG. 5B is another representative side view of a flexible piercing needle of the drug delivery devices of the present invention.

FIG. 5C is a representative section view of a distal end portion of a drug delivery device such as shown in FIGS. 4A–4D.

FIG. 6A is a representative internal view of a tubular viewing assembly having a controllable distal tip.

FIG. 6B is another representative internal view of a tubular viewing assembly having a controllable distal tip.

Figure 1A:
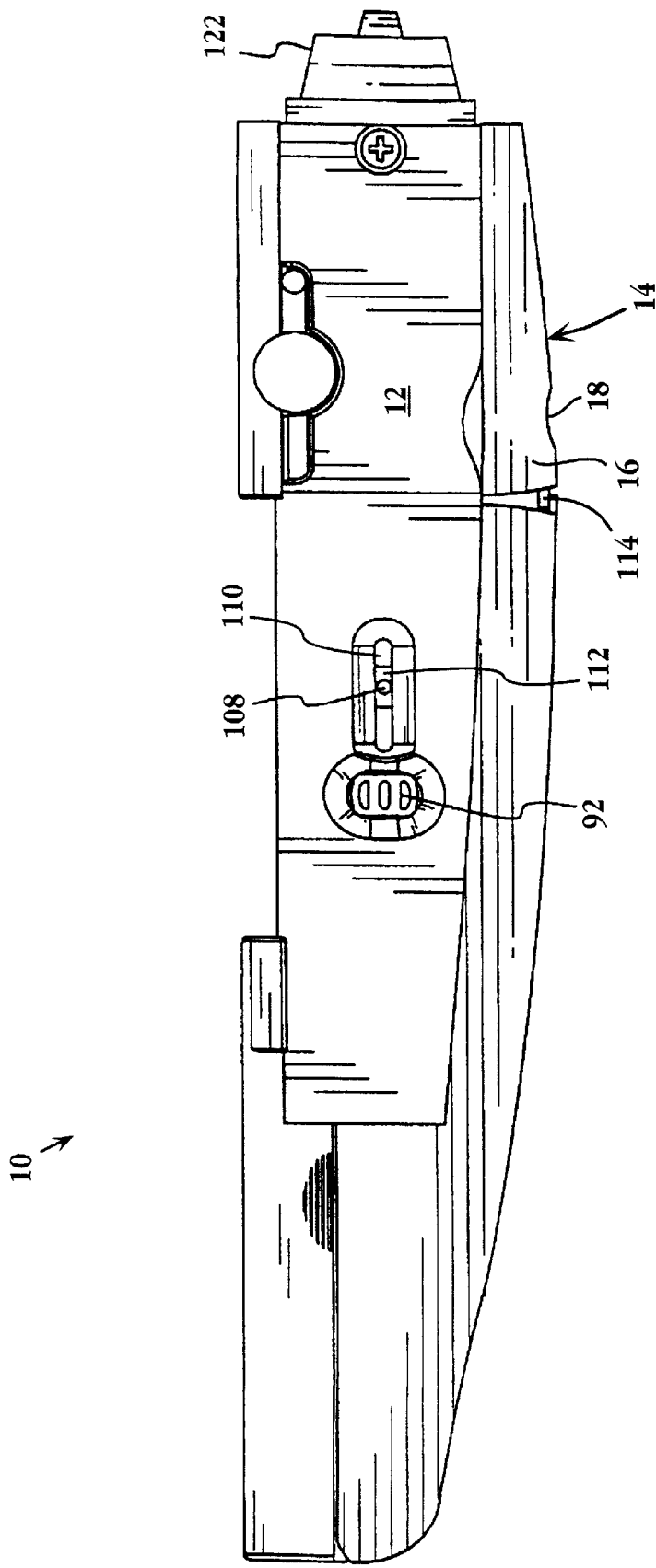
FIG. 1A is a representative side view of a preferred embodiment of a drug delivery module (DDM) of the present invention.
Figure 1B:
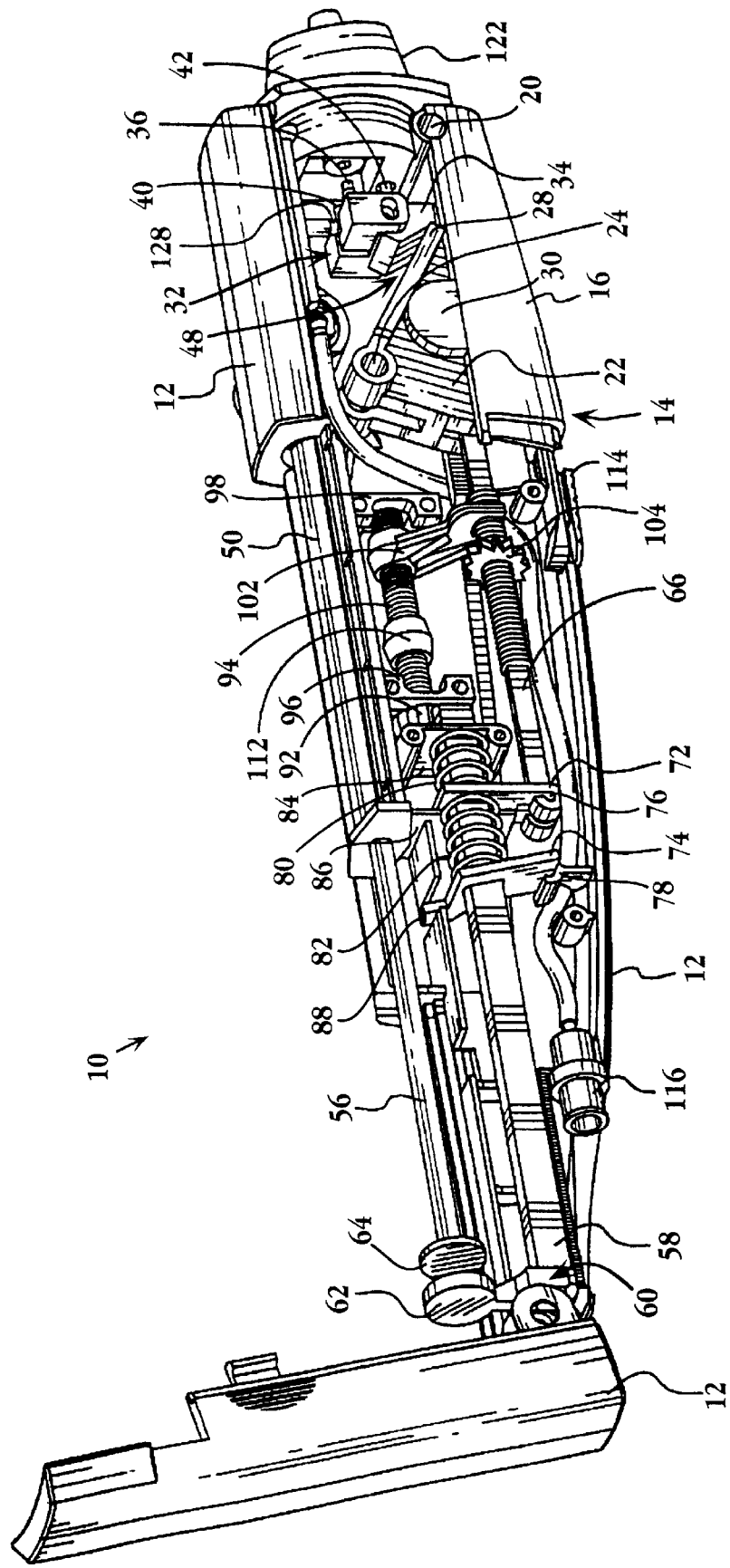
FIG. 1B is a representative isometric view of a delivery module (DDM) such as shown in FIG. 1A.

It will be understood that the invention's preferred embodiments have many of the individual elements whose functional aspects are similar. Thus, it will be understood that structural elements having similar or identical functions may have like reference numerals associated therewith. The appended drawings illustrate only typical embodiments of this invention and are therefor not to be limiting of its scope, for the invention may admit to other equally effective embodiments.

DETAILED DESCRIPTION OF THE INVENTION

A minimally invasive penetration in the chest is significantly different than "open heart" or "open chest" surgery, i.e. the gross spreading of the ribs or cutting through ribs and/or the sternum. Minimally invasive surgery (MIS) involves formation of penetrations that may be performed intercostally or non-intercostally. Metering of drug entails delivering precise amounts of recombinant formulations, such as, angiogenic growth factors to expedite and/or augment collateral artery development.

Drugs that need frequently repeated administration over longer periods of tine could require repeated hospitalizations or clinic visits—an exception to this is in the case of cancer chemotherapy, where the patient normally goes to the hospital for drug administration in the course of routine treatment. In the case of a drug administered to the heart, where blood circulation may cause a rapid clearance of any therapeutic delivered in or near the channels, the drug would need a time course of action that is rapid enough to have effect before it is cleared.

One set of applications of such drug delivery involve certain antibody treatments, where it is desirable to target the antibody to the area of intended treatment in order to achieve the highest possible local concentration of a relatively extremely expensive reagent. For example, in enzyme-linked antibody therapy currently under investigation in the treatment of certain cancers, an enzyme linked to an antibody specific to a tumor is delivered and allowed to bind to the tumor cells.

Thus, two applications for which the drug delivery module of the present invention is especially adapted are (1) delivery of angiogenic factors alone or in conjunction with cardiac procedures and (2) delivery of a chemotherapeutic to a solid tumor, in a variety of applications including either before or after a laser is used to ablate tumor tissue, before or after systemic drug treatment, etc. A normally toxic chemotherapeutic such as doxorubicin or taxol that is made systemically non-toxic by being modified to a prodrug is injected into the tumor. The drug would remain non-toxic until it meets the enzyme linked to the antibody, where the prodrmg is converted into active drug. In this way, higher local concentrations of the drug could be created near the tumor than would be possible by traditional chemotherapy, where systemic toxicity is the limiting factor.

Scope of Drug Therapy

Therapeutics which may be advantageous to deliver through a drug delivery device can be broadly placed into five overlapping therapeutic categories:

1) agents which act on the blood clot cascade,
2) agents that mediate inflammation or cell adhesion/recognition processes,
3) agents which have an effect on the cardiovascular system,
4) agents that may be used in the treatment of cancer, and
5) agents used for angiogenesis and gene therapies.

These categories are broadly overlapping, so that many agents will fall into more than one category. Antibody agents, for example, may appear in all five categories. Certain growth inhibitors can be used for anti-cancer treatment as well as for the treatment of other disease processes. Agents named in the following charts are illustrative and are not meant to be a comprehensive listing of all agents available for the given therapeutic category. Agents appearing as examples in one category may have uses in other therapeutic categories. It will be understood that there are additional categories which may become useful, such as agents directed at bone or implanted in semi-permeable sacs, radioisotopes, and future gene therapies.

Photodynamic therapy is another important delivery and dosing method. Drugs or other compounds which have certain therapeutic or other activity or function can be regulated using such technology. Photo-active or photo-labile compounds are those whose activity or function is controlled by light energy. While the use of sensitizing agents or protective groups to block activity of the drug or other compounds in topically applied formulations is known, the use of such protective groups is unknown in conjunction with drugs delivered for angiogenic purposes or in conjunction with cardiac procedures.

"Caged" compounds are compounds which have a photo-active reagent which masks the original characteristics of the compounds. Thus, these caged or otherwise photo-labile compounds can be delivered to the target tissue or target region in a pharmacologically inactive form. Upon irradiation with laser energy or other, operative electromagnetic radiation, the protective group or groups are caused to be rendered inert, thereby initiating therapeutic activity. These photoactive protective groups or "cage" molecules are especially useful in conjunction with highly toxic drugs or marker substances. For example, chemotherapeutic agents are particularly toxic and, thus, their toxicity can be eliminated until the agent is delivered to the precise region of the body where it's toxicity will be most effectively and safely used. Irradiation of the photo-labile compound with light energy of a suitable wavelength, frequency and duration can then render the drug or other photo-labile agent active.

Dosing

Active compounds which are given systemically have a normal therapeutic window which can be expressed as mg of drug per kg of body weight. The amount of agent which is therapeutically acceptable when administering a drug locally can be approximated as mg of drug per kg of target treatment area (e.g. organ weight), optimized accordingly with consideration of toxicity and mechanism of drug action.

Agents delivered to a specific site can achieve high local concentrations at the delivery point. Optimal drug dose may scale differently when the drug is administered locally rather than systemically. Thus, the amount of a given agent that should be delivered in order to achieve a therapeutic effect must be optimized accordingly with consideration of toxicity levels (both locally and systemically), mechanism of drug action, drug clearance mechanisms, and drug diffusion levels.

Category 1

Examples of Azents Which Have an Effect on the Blood Clot Cascade

These agents work by either promoting or inhibiting blood clot cascade pathways. These agents are actual blood clot cascade participants, which mimic actual blot clot cascade participants, or agents which act as enzymes or inhibit enzymes that are associated with the blood clot cascade. Some examples of agents in these categories include:

| Category | Agent | Manufacturer | Indication | Form |
|---|---|---|---|---|
| Anticoagulant Antagonists | Protamine Sulfate | Eli Lilly | treatment of heparin overdosage | IV |
| Anticoagulants | Heparin | Wyeth-Ayerst | prophylaxis and treatment of venous thrombosis; prevention of post-operative deep venous thrombosis and pulmonary embolism; prevention of clotting in arterial and cardiac surgery; prophylaxis and treatment of peripheral arterial embolism | IV |
| Antifibrinolytic | Amicar (aminocaproic acid) | Immunex | enhances hemostasis when fibrinolysis contributes to bleeding | IV/oral |
| Platelet Inhibitors | ReoPro (abciximab) | Eli Lilly | adjunct to percutaneous transluminal coronary angioplasty or atherectomy (PTCA) for the prevention of acute cardiac ischemic complications in patients at high risk for abrupt closure of the treated coronary vessel | IV |
| Thrombolytics | Activase (alteplase, TPA) | Genentech | management of acute myocardial infarction in adults, management of acute massive pulmonary embolism in adults | IV |

Category 2

Examples of Agents That Mediate Cell Adhesion and/or Cell Recognition Processes

These agents act on cell signaling pathways and recognition processes, and includes receptor agonists and antago nists. A subset of these agents mediate inflammation and the immune response. Some examples of agents in the category include:

| Category | Agent | Manufacturer | Indication | Form |
| --- | --- | --- | --- | --- |
| Antihistamines | Seldane (terfenadine) | Marion Merrell Dow | relief of symptoms associated with seasonal allergic rhinitis | oral |
| Anti-Inflammatory Agents | Toradol (ketorolac tromethamine) | Roche Laboratories | short-term (<5 days) management of moderately severe, acute pain that requires analgesia at the opioid level | IV/IM/oral |
| Immuno-suppressives | Sandimmune (cyclosporin) | Sandoz | prophylaxis of organ rejection in kidney, liver, and heart allogeneic transplants; also in the treatment of chronic rejection in patients previously treated with other immunosuppressive agents | IV/oral |
| Receptor Antagonists | Tagamet (cimetidine hydrochloride) | Smith Kline Beecham | management of ulcers, erosive gastroesophageal reflux disease, prevention of upper gastrointestinal bleeding in critically ill patients, treatment of pathological hypersecretory conditions | IV/IM/oral |

Category3
Examples of Cardiovascular Agents

These agents work at various points in the cardiovascular and associated systems. Angiogenic factors and anti-angiogenic factors appear in this category as well as in the cancer therapeutics category. Some examples of agents in the category include:

| Category | Agent Name | Manuracturer | Indication | Form |
| --- | --- | --- | --- | --- |
| Adrenergic Blockers | Minipress (prazosin hydrochloride) | Pfizer | treatment of hypertension | oral |
| Adrenergic Stimulants | Aldomet (methyldopate HCl) | Merck | treatment of hypertensive crisis | IV |
| Alpha/Beta Adrenergic Blockers | Normodyne (labetalol HCl) | Schering | control of blood pressure in severe hypertension | IV |
| Angiotensin Converting Enzyme Inhibitors | Capoten (captopril) | Bristol-Myers Squibb | treatment of hypertension | oral |
| Angiotensin II Receptor Antagonists | Cozaar (losartan potassium) | Merck | treatment of hypertension | oral |
| Antiarrhythmics Group I | Norpace (disopyramide phosphate) | Searle | treatment of documented ventricular arrhythmias, such as sustained ventricular tachycardia | oral |
| Antiarrhythmics Group II | Brevibloc (esmolol hydrochloride) | Ohmeda | rapid control of ventricular rate in patients with atrial fibrillation or atrial flutter in perioperative, postoperative, or other emergent circumstances where short term control of ventricular rate with a short-acting agent is desired; indicated in noncompensatory sinus tachycardia where the rapid heart rate requires specific intervention; indicated of the treatment of tachycardia and hypertension that occur during induction and tracheal intubation, during surgery, on emergence from anesthesia, and in the postoperative period | IV |

-continued

| Category | Agent Name | Manufacturer | Indication | Form |
|---|---|---|---|---|
| Antiarrhythmics Group III | Cordarone (amiodarone HCl) | Wyeth-Ayerst | treatment and prophylaxis of frequently recurring ventricular fibrillation and hemodynamically unstable ventricular tachycardia in patients refractory to other therapy | IV/oral |
| Antiarrhythmics Group IV | Cardizem (diltiazem HCl) | Marion Merrell Dow | IV: indicated for atrial fibrillation or atrial flutter and paroxysmal supraventricular tachycardia oral: treatment of hypertension and management of chronic stable angina and angina due to coronary artery spasm | IV/oral |
| Beta Blockers | Inderal (propranolol HCl) | Wyeth-Ayerst | management of hypertension, management of angina pectoris due to coronary atherosclerosis, management of cardiac arrhythmias, indicated to reduce cardiovascular mortality in patients who have survived the acute phase of myocardial infarction and are clinically stable, prophylaxis of the common migraine headache | IV/oral |
| Calcium Channel Blockers | Procardia (nifedipine) | Pratt Pharmaceuticals | management of vasospastic angina, chronic stable angina, and hypertension | oral |
| Diuretics | Bumex (bumetanide) | Roche | treatment of edema associated with congestive heart failure, hepatic and renal disease, including nephrotic syndrome | IV/IM/oral |
| Hypertensive Emergency Agents | Hyperstat (diazoxide) | Schering | short term use in the emergency reduction of blood pressure in severe, non-malignant and malignant hypertension | IV |
| Growth Factors | Vascular Endothelial Growth Factor (VEGF) (preclinical) | Genentech | promotes angiogenesis; still experimental | pre-clinical |
| Inotropic Agents | Lanoxin (digoxin) | Glaxo Wellcome | management of heart failure, atrial fibrillation, atrial flutter, paroxysmal atrial tachycardia | IV/oral |
| Patent Ductus Arteriosus Therapy | Indocin (indomethacin sodium trihydrate) | Merck | indicated to close a hemodynamically significant patent ductus arteriosus in premature infants | IV |
| Rauwolfia Derivatives & Combinations | Diupres (reserpine-chlorothiazide) | Merck | hypertension | oral |
| Vasodilators | Nitrostat (nitroglycerin) | Parke-Davis | prophylaxis, treatment, and management of patients with angina pectoris | oral |
| Vasopressors | Vasoxyl (methoxamine hydrochloride) | Glaxo Wellcome | supporting, restoring, or maintaining blood pressure during anesthesia | IV |

Category 4

Examples of Cancer Therapeutics

Cancer therapy can proceed along several different lines, all of which seek to kill or limit the growth of cancer cells while doing minimal damage to the host. Thus, any difference in cancer cell properties (e.g. metabolism, cell-surface antigen presentation) from healthy host cells is a target for exploitation. With the local administration of therapeutics, these differentiating factors may be created and/or exploited. For example, the local administration of cytotoxins or growth inhibitors may allow higher local concentrations of the compounds than would be achievable by systemic administration. Differences in cell-surface recognition molecules may be a site for antibody therapy. Differences in tumor morphology are also potential sites of intervention: for example, anti-VEGF may be useful in retarding the vascularization of the interior of a solid tumor, thereby slowing its growth rate. Some examples of agents in the category include:

| Category | Agent Name | Manufacture | Indication | Form |
|---|---|---|---|---|
| Adjuncts | Kytril (granisetron HCl) | Smith Kline Beecham | prevention of nausea and vomiting associated with emetogenic cancer therapy, including high-dose cisplatin | IV |
| Androgen Inhibitors | Lupron (leuprolide actetate) | TAP Pharmaceuticals | palliative treatment of prostatic cancer | IM |
| Antibiotic Derivatives | Doxorubicin Hydrochloride | Astra USA | produces regression in disseminated neoplastic conditions and possibly some solid tumors | IV |
| Antiestrogen | Nolvadex (tamoxifen citrate) | Zeneca Pharmaceuticals | treatment of metastatic breast cancer | oral |
| Antimetabolites | Roferon-A (interferon alfa-2a) | Roche | treatment of hairy cell leukemia and AIDS-related Kaposi's sarcoma | IM/SC |
| Cytotoxic Agents | Taxol | Bristol-Myers Squibb | treatment of metastatic carcinoma of the ovary and treatment of breast cancer | IV |
| Enzyme Inhibitors | Ras farnesyl-transferase inhibitor (preclinical) | Genentech | treatment of pancreatic and colon cancers | pre-clinical |
| Hormones | Depo-Provera (medroxy-progesterone acetate) | Upjohn | adjunctive therapy and palliative treatment of inoperable, recurrent, and metastatic endometrial or renal carcinoma | IV |
| Immuno-modulators | Proleukin (aldesleukin) | Chiron | treatment of metastatic renal cell carcinoma | IV |
| Nitrogen Mustard Derivatives | Alkeran (melphalan HCl) | Glaxo Wellcome | treatment of multiple myeloma | IV/oral |

Category 5
Angiogenic Factors and Agents Used in Gene Therapies

There are two recognized mechanisms for formation of new blood vessels, these are vasculogenesis—the formation of vessels through aggregation of endothelial cells, and angiogenesis—the growth of new vessels from pre-existing vessels. Vasculogenesis is particularly critical during development of the embryo. Angiogenesis, while important in development, also occurs in the adult during, for example, wound healing and ovulation. New blood vessel growth is also a critical phase of solid tumor growth—without a new blood supply tumors cannot grow more than about 1–2 mm in diameter. Differential cDNA screening is currently being used to identify genes involved in tube formation, a critical process in the development of a blood vessel.

Since some cardiac procedures create injuries, and induce secondary vascularization, whatever signal is given to induce vascularization could be pharmacologically amplified. Mechanisms for this type of induced revascularization may stem from factors induced by tissue damage (VEGF or other growth-factor derived response, or perhaps heat-shock proteins produced by thermal damage caused by a laser). Regardless of the actual mechanism, an angiogenic factor used in conjunction with cardiac procedures such as CABG or TMR may increase the effectiveness of the technique.

A preferred one of the angiogenic factors commonly available (e.g. VEGF, FGF-1, FGF-2, EGF) is VEGF, vascular endothelial growth factor. VEGF has been shown to be effective in improving vascularization in the rabbit ischemic hindlimb model after a single bolus administration. VEGF also has a serum half life of less than 6 minutes (unpublished results), and certain isoforms of VEGF have the property to bind to the cell surface—i.e. VEGF may not need to be present for very long in order to have an effect. Thus, it is possible to apply VEGF in or near injury sites to increase the revascularization of ischemic myocardium.

Basic fibroblast growth factor (bFGF), also known as FGF-2, is another possible angiogenic agent. There is some indication that VEGF and bFGF used together are more effective than either one alone.

Drug Delivery Module (DDM)

In one general embodiment, the drug-delivery module, or device, of the present invention includes a housing with an actuator mounted thereon for movement between open and closed positions, and a carriage assembly mounted therein for movement between retracted and extended positions. The carriage assembly includes a linkage connectable to a needle for needle movement with the carriage assembly between retracted and extended needle positions. One or more fluid reservoirs are adapted for fluid connection to the needle. Advancing means operatively connect the actuator to the carriage assembly, to advance the assembly toward its extended position when the actuator is moved from its open position, toward its closed position. Compressing means operatively connect the actuator to the reservoir for compressing the reservoir when the actuator is moved from its open position toward its closed position.

Several exemplary embodiments of the device will now be described. For clarity of description, it should be noted that the exemplary devices are depicted with their forward regions generally toward the right in the drawings, and their rearward regions toward the left.

In the exemplary embodiment of FIGS. 1A–1E, the delivery device of the invention, indicated generally by the reference numeral 10, includes a housing 12 configured to be held and manipulated by an operator, such as a surgeon or cardiologist. Particularly, housing 12 is designed to be grasped like a wand, stick, or pistol with the operator's thumb extending over the top of the housing and four fingers wrapped about the lower side of the device.

Housing 12 can be constructed of any suitable material by any conventional means. For example, the housing can be formed from a plurality of separately formed panels or sections, molded of an impact resistant plastic material or the like, and assembled by way of threaded fasteners, snap-fitting portions, and/or other conventional techniques.

An actuator, denoted generally as 14, is mounted on housing 12 for movement between open and closed positions. Particularly, actuator 14 includes a manually operable handle 16, in the nature of a trigger, mounted at its forward end at a pivotal connection 20 in a forward, lower region of housing 12. Handle 16 is adapted for movement between a normal, open position, projecting downwardly and outwardly from housing 12, and a closed position, compressed (squeezed) upwardly and inwardly toward the housing. A recessed or depressed region 18 along a lower side of handle 16 is configured to accommodate the index finger of an operator for manual actuation, and can include grip-enhancing structure (e.g., raised ridges or bumps) thereon (not shown).

Actuator 14 fuirther includes a pivoting member 22 mounted in hotusing 12 for pivoting movement in forward and reverse directions, as handle 16 is moved toward and away from its closed position, respectively. In this regard, pivoting member 22 is attached at its upper end in housing 12 at a pivot connection 24 for pivotal movement thereabout. Movement of pivoting member 22 is effected by sliding contact between upper regions of handle 10 at a location inside housing 12, with confronting portions of pivoting member 22. Particularly, as best viewed in FIGS. 1B and 1D, pivoting member 22 is provided with side wings, or lateral extensions, denoted as 26 and 28 (FIG. 1D), each having a generally flat, smooth undersurface. Handle 16, in turn, includes an upstanding protrusion on each lateral side—only one of which is visible in FIGS. 1B and 1D, denoted as 30 - with each such protrusion being adapted to engage, along its upper edge, the lower surface of a respective lateral extension. By this construction, as handle 16 is moved from its open position toward its closed position, its upstanding protrusions slidingly engage the lateral extensions of pivoting member 22, thereby urging the pivotal member to move forwardly, about pivot connection 24. As handle 16 returns to its open position, pivoting member 22 moves in a reverse direction.

A carriage assembly, indicated generally as 32, is mounted in housing 12, forwardly of pivoting member 22, for movement between retracted and extended positions. Carriage assembly 32 includes a main body portion 34, with a linkage 36 extending forwardly from a front face thereof. As described more fully below, linkage 36 is connectable to a remote (distal) needle, such as at 186 in FIG. 3A, for needle movement with carriage assembly 32 between retracted and extended needle positions. Carriage assembly 32 further includes a pair of guide rods, denoted as 40 and 42 (FIG. 1B), which also extend from the front face of body 34. Each guide rod is slidably received within a respective bore extending into a front region of the device. Sliding movement of the guide rods within their respective bores defines the pathway along which the carriage assembly can travel, as it is moved between its retracted and extended positions. A coil spring, such as 44, is concentrically mounted over at least one of the guide rods (e.g., guide rod 42 in FIG. 1E), to normally urge carriage assembly 32 to its retracted position.

Movement of carriage assembly 32 is effected by the action of actuator 14. In this regard, advancing means operatively connect the acuator to the carriage assembly, to advance the carriage assembly toward its extended position when the actuator is moved from its open position, toward its closed position. In the present embodiment, the advancing means includes a sliding surface contact between a forward edge of pivoting member 22 and a back-angled portion of the back face of carriage-assembly body 34, along the regions denoted generally at 48. Thus, the back-angled portion of carriage-assembly body 34 acts as a cam surface against which the forward edge of pivoting member 22, functioning here as a camn, can act. By this construction, as pivotal member 22 moves along its forward direction, its forward edge engages, and slides upwardly along, the back-angled rearward face of carriage-assembly body 34, such that, upon overcoming the force of spring 44, carriage assembly 32 is pressed forwardly, toward its extended position.

Figure 3A:
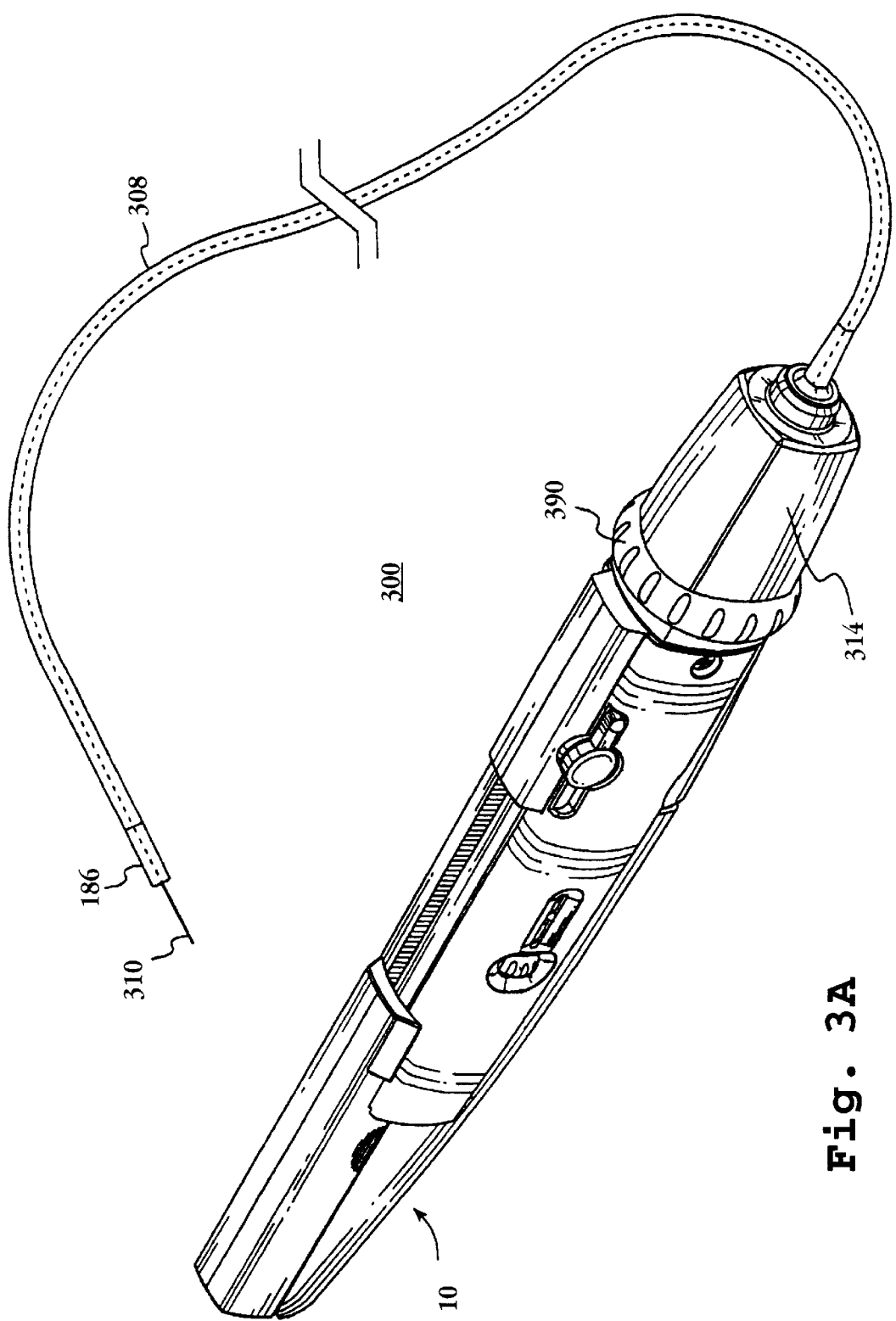
FIG. 3A is a representative isometric view of a modular or unitary catheter-type drug delivery device of the present invention.
Figure 3B:
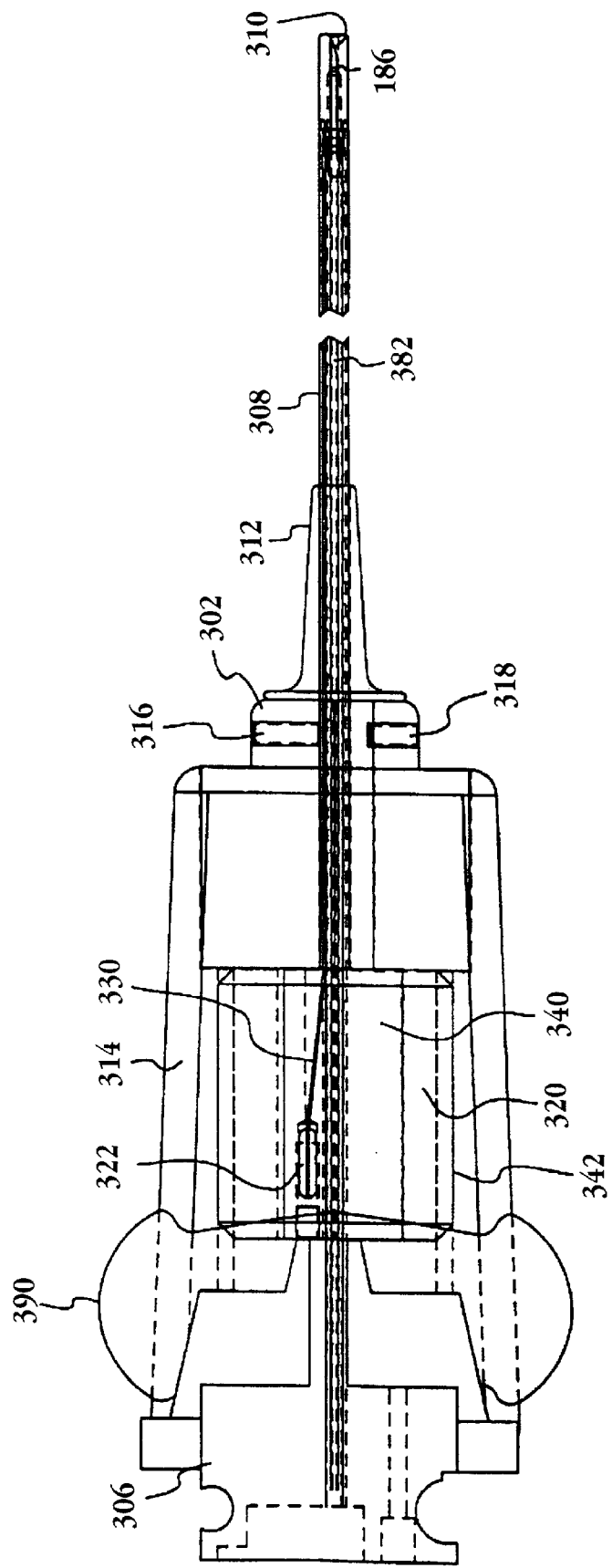
FIG. 3B is a representative partial section view of a control portion modular or unitary catheter-type drug delivery device of the present invention.

A fluid reservoir, e.g., a syringe, vial or cartridge reservoir, is adapted for fluid connection to a remote (distal) needle, such as needle 186 in FIG. 3A. In the drawings, the fluid reservoir is a syringe barrel, denoted as 50, removably mountable within an upper portion of housing 12. Syringe barrel 50 includes an outlet 52 portion (FIGS. 1C and 1E) at its forward end that can be connected in fluid communication with the remote needle, as described below. Prior to being mounted in housing 12, syringe barrel 50 can be loaded with a selected fluid, such as an agent, solvent, carrier, purging fluid, hydraulic fluid, or other substance, as desired. Barrel 50 is adapted to hold such fluid until such time that a delivery operation is carried out.

Compressing means operatively connect the actuator to the reservoir for compressing the reservoir when the actuator is moved from its open position, toward its closed position. In the illustrated arrangement, the compressing means includes a plunger 56, with the plunger being slidably disposed within syringe barrel 50 for movement toward outlet 52, to expel fluid from the reservoir. Such movement of plunger 56 is effected by forward movement of a sliding bar, denoted as 58, disposed generally co-extensive with the housing's central, longitudinal axis and operatively engageable at one bar end with plunger 56. In this regard, a plunger drive 60 is rigidly mounted at a rearward end of sliding bar 58. Plunger drive 60 includes an upstanding paddle portion, denoted as 62, with a front face confronting an enlarged head 64 at the rearward end of plunger 56. As is evident in the figures, paddle portion 62 of plunger drive 60 will push upon enlarged head 64 of plunger 56 as sliding bar 58 is moved forward.

Forward movement of sliding bar 58 is effected by movement of actuator 14 toward its closed position, via a reciprocating bar 66 extending longitudinally along a lower region of housing 12 and operatively interconnecting actuator 14 and sliding bar 58. Particularly, a forward end of reciprocating bar 66 is pivotally connected to a lower, rearward portion of pivotal member 22 via a pivot-pin connection, as at 68 (FIGS. 1C and 1E). Thus, forward movement of pivotal member 22, as effected by movement of handle 16 toward its closed position, is effective to pull, or drag, reciprocating bar 66 in a forward direction. At its rearward end, reciprocating bar 66 is operably coupled to sliding bar 58 via a releasable locking mechanism, indicated generally at 70 in FIG. 1E (described next), such that successive actuations of actuator 14 are effective to advance sliding bar 58 incrementally in a forward direction effective to expel a defined and incremental quantity of fluid from the reservoir (here, barrel 50) with each such actuation.

The locking mechanism includes first and second pivot plates, denoted as 72 and 74, respectively. A lower region of first plate 72 is coupled to a rearward end of reciprocating bar 66 via a pivot-pin connection, as at 76, or other pivot-connection mechanism. A bore is forned through an upper region of first plate 72, through which sliding bar 58 is passed - as shown, for example, in FIG. 1D. A lower end of second plate 74 is adapted for pivotal motion in a U-shaped pivot mount, denoted as 78 in FIGS. 1B and 1C, formed in housing 12 adjacent (below) sliding bar 58. As shown in the figures, second plate 74 is disposed rearwardly of, and in spaced relation to, first plate 72. Like the first plate, second plate 74 includes a bore through its upper region, through which sliding bar 58 is passed. First and second coil springs, denoted as 80 and 82, respectively, are mounted over sliding rod 58, with (i) the first spring 80 compressed between a front face of first plate 72 and a rearward face of a first stop member 84 (FIGS. 1B and 1C) formed in housing 12 forwardly of first plate 72, and (ii) second spring 82 compressed between a front face of second plate 74 and a rearward face of a second stop member 86 formed in housing 12 forwardly of second plate 74, and rearwardly of first plate 72. Notably, a rearward, upper portion of first plate 72 is urged by spring 80 toward a forward face of second stop member 86. In operation, first plate 72 engages or releases sliding bar 58, as reciprocating bar 66 is advanced in a forward or reverse direction, respectively; and second plate 74 releases or engages sliding bar 58 as reciprocating bar 66 is advanced in a forward or reverse direction, respectively.

Additional details of the above components, as well as the relative timing of the various motions effected by actuation of the device, are revealed by the following summary of certain aspects of a typical actuation operation. When actuator 14 is moved from its open position, toward a position intermediate its open and closed positions (such range of movement being referred to herein as "early" actuator movement), the advancing means is effective to advance carriage assembly 32 toward its extended position, as previously described. During such early actuator movement, however, no reservoir compression takes place. This is because, notwithstanding the fact that reciprocating bar 66 is pulled in a forward direction during such early actuator movement, such early movement is not transmitted to sliding bar 58. In this regard, first pivot plate 72 acts a motion buffer or absorber, effectively shielding sliding bar 58 from such early movement. In this regard, it should now be recalled that the first pivot plate's upper end is urged toward the forward face of the second stop 86 by first coil spring 80. Thus, as pivoting member 22 pulls the first plate's lower end forwardly, and spring 80 maintains its upper end at a rearward position, first plate 72 is caused to tilt back during early movement of the actuator. Sliding bar 58 is not pulled forwardly as first plate 72 tilts back. This buffering effect, however, is effective only for movement of actuator 14 up to a certain, predetermined intermediate position. Beyond such intermediate position, as the actuator moves from such intermediate position toward its closed position (referred to herein as "late" actuator movement), the upper and lower edges of the first plate's bore engage the upper and lower edges of sliding bar 58, respectively, so as to grab the bar and drag it forward. As previously described, forward movement of the sliding bar effects reservoir compression. It should be noted that the second plate does not resist movement of the sliding bar in the forward direction.

During most, or all, of the compression operation, which, as described above, generally takes place only during late actuator movement, little, if any, further advancement of the carriage assembly takes place. This is because the camming that takes place via sliding surface contact between pivoting member 22 and carriage assembly 32 is substantially completed once the actuator is reaches its intermediate position, from its open position. In this regard, attention is directed to FIGS. 1B–1E, where it can be seen that the back-angled portion along the rearward face of carriage-assembly body 34 extends only up to a certain point. The forward edge of pivoting member 22 reaches this terminal point on the body's back face as the actuator reaches its intermediate position. Thus, no further camming can take place as the actuator is moved beyond its intermediate position toward its closed position.

From its closed position, the actuator will typically be allowed to return to its open position. During such return movement, reciprocating bar 66 moves in a reverse (backward) direction, with reverse movement of the actuator's pivoting member 22. As the reciprocating bar moves back, first plate 72 slides back along sliding bar 58, and returns to its normal, substantially upright orientation. Notably, second plate 74 does not permit reverse movement of sliding bar 58 (except when a force is applied that tilts the second plate forwardly—e.g., as by manually pressing in a forward direction on an upstanding release tab 88 (FIGS. 1B and 1D) extending from the top of the second plate). Also, as the actuator's pivoting member moves in a reverse direction, the forward edge of the pivoting member slides downwardly along the back-angled portion of the rearward face of the carriage-assembly body, permitting the carriage to return to its retracted position under the bias of spring 44.

From the above description, it should be appreciated that the illustrated device provides controlled needle advance, followed by rapid fluid (e.g., agent) delivery—with a single sweep of the actuator from its open position to its closed position.

Optionally, means can be provided for selectably adjusting the volume displaced in the reservoir (e.g., syringe barrel 50) by the compressing means with each actuation of actuator 14. Such means can be useful, for example, to select an amount of fluid to be expelled from the reservoir with each actuation. In the embodiment of FIGS. 1A–1E, for example, a displacement-volume-adjustment thumbwheel 92 provides an externally accessible interface permitting an operator to readily adjust the reservoir displacement volume. Particularly, thumbwheel 92 is co-axially and rigidly fixed about a rearward region of an externally threaded shaft 94 which, in turn, is mounted for rotation within housing 12 in spaced-apart support members, 96 and 98, extending off an interior sidewall thereof. A stop arm 102 is threadedly mounted at one (upper) end along a forward region of shaft 94, such that rotation of shaft 94 will cause stop arm 102 to move in a forward or reverse direction, longitudinally within housing 12, dependent upon the particular direction of shaft rotation. The other (lower) end of stop arm 102 is configured generally in the shape of an inverted U, which straddles a forward region of reciprocating bar 66. An internally threaded, wide-diameter stop nut 104 is mounted on an externally threaded region of reciprocating bar 66, rearwardly of the stop arm's U-shaped portion. In operation, forward movement of reciprocating bar 66 brings a front face of stop nut 104 into abutting contact with a rearward side of the stop arm's U-shaped portion, thereby prohibiting further forward motion of reciprocating bar 66. By rotating shaft 94 in an appropriate direction (via thumbwheel 92), stop arm 102 can be moved to a desired position alongside reciprocating bar 66. In this way, the length of travel available for forward movement of the reciprocating bar, and, thus, the length of plunger travel in the reservoir, can readily be set.

Figure 1C:
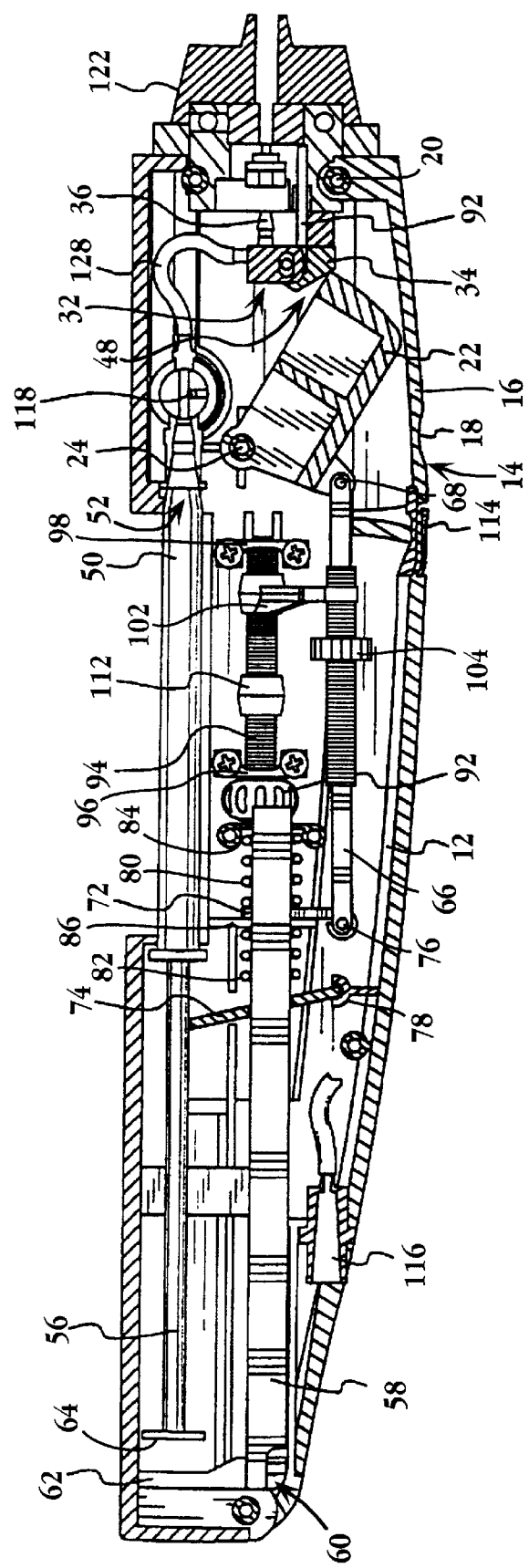
FIG. 1C is a representative section view of a drug delivery module such as shown in FIG. 1A.
Figure 1D:
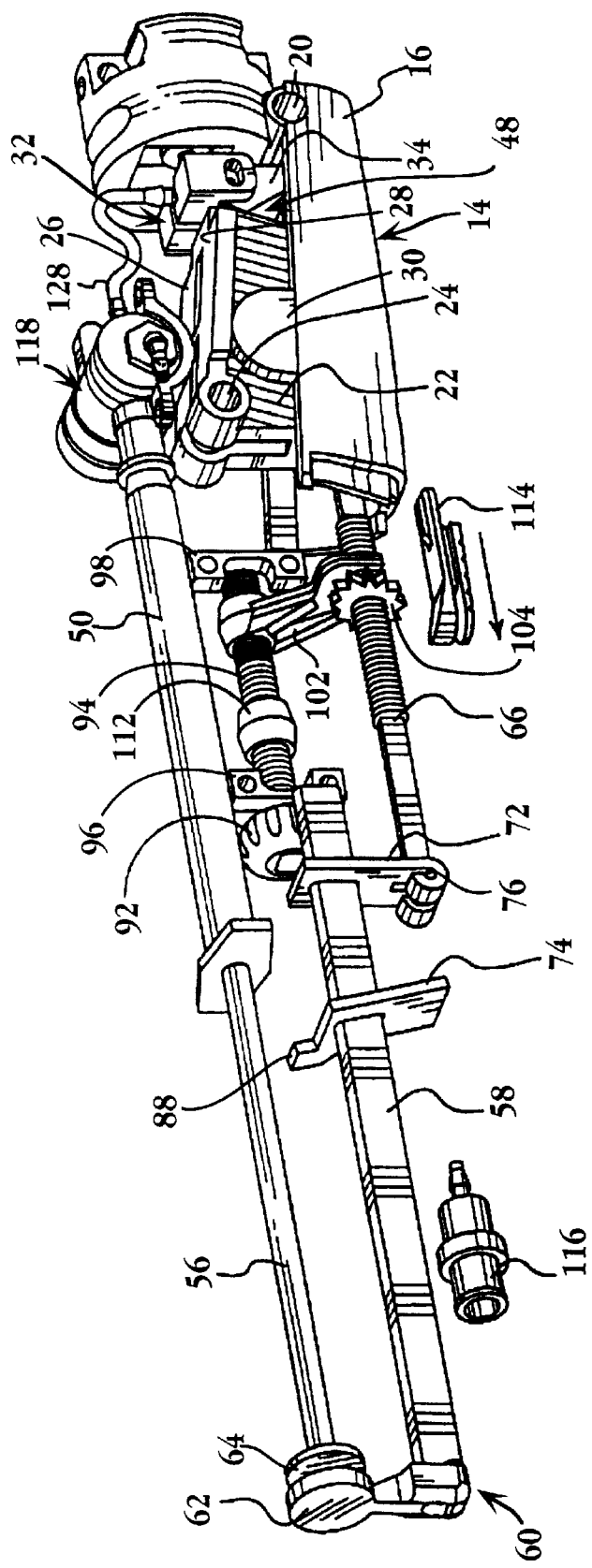
FIG. 1D is a representative internal view of a drtig delivery module such as shown in FIG. 1A.
Figure 1E:
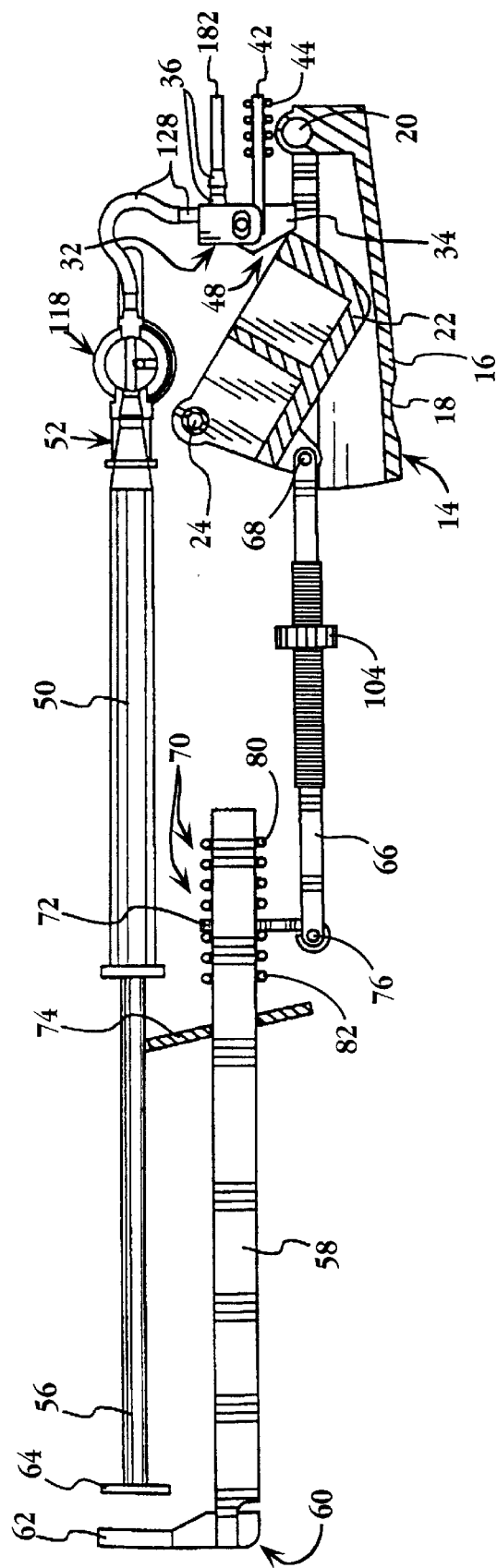
FIG. 1E is a representative detail view of a drug delivery module such as shown in FIG. 1A.

An indicator, or pointer, denoted as 108 in FIG. 1A, is viewable through an elongate window 110 formed longitudinally along one side of housing 12, adjacent shaft 94. Indicator 108 is provided on an annular ring 112, which is also threadedly mounted on shaft 94. As shaft 94 is rotated via thumbscrew 92, indicator 108 is caused to move longitudinally along shaft 94, in a forward or reverse direction, dependent upon the direction of shaft rotation. The position of indicator 108 at any given time indicates a particular, corresponding position of stop arm 102 along shaft 94. In this way, the indicator provides an externally visible means of determining the position of the stop arm, without having to directly view the stop arm itself. Knowing the position of the stop arm, one can also determine the reservoir volume that will be displaced upon actuation. To this end, a scale (not shown) can be imprinted or molded along the exterior of housing 12, e.g., alongside window 110, to provide quantitative volume information to an operator. For example, a double scale can be printed on the housing with both 0.01–0.1 cc scaled markings and 0. 1–0.3 cc scaled markings, permitting convenient selection and setting of the desired displacement volume. The scale ranges can be modified as desired, depending upon the application, type of fluid to be delivered, and/or other determinants.

A safety switch, or lock, can be provided, for locking the delivery device against inadvertent actuation, when desired. For example, FIGS. 1A–1D show a slider-type, safety lock 114 that, when shifted to a forward position, locks the handle in its open position. In this way, actuation is not permitted. Upon depressing the safety lock and sliding it in a backward direction (as shown by the arrow in FIG. 1D), the handle is unlocked, thereby permitting actuation.

Delivery device 10 is also provided with a saline or other solution flush connector 116 (FIGS. 1B–1D), which can be a standard Luer-type fitting, or other standard or proprietary connector. Typically, sterile bags of saline, vessels, canisters or other reservoirs are suspended to provide gravity feed, or the bags or other reservoirs can be pressurized or the fluid otherwise pumped out. A standard section of tubing or other tubular section (not shown) communicates fluid, other material or vacuum through flush connector 116 to a valve assembly 118 disposed at a forward, upper region of the device.

In the present embodiment, valve 118 includes two inlets and one outlet. Using any suitable tubing or other fluid-connection devices, valve 118 is configured to permit the establishment of fluid communication between its outlet and (i) connector 116 (e.g., for flush-solution flow), as well as (ii) reservoir 50 (e.g., for agent, or other fluid, flow). Preferably, such connections with the valve's outlet can be established alternatively, one at a time; or simultaneously, as desired. An alternative embodiment contemplates a valve having two outlets. This can be useful, for example, where it is desired to direct flush solution to more than one downstream location.

It will also be understood that a second, third, pseudo, modified or other additional reservoirs containing drug, saline, flush or other solution or material may also be linked or coupled to port 116. Thus, valve 118 may be replaced with a manifold-type system for coupling of multiple internally or externally located reservoirs of different drugs or other materials. Device 10 will optionally, therefore, provide delivery with or without pre-mixing or mixing, such as at site of delivery, and with the potential for providing sequential and/or simultaneous administration of drug, medication or other material internally.

The delivery device 10 of the invention is particularly well suited for use in connection with a medical appliance, such as an endoscope or a catheter-type assembly. Briefly, such appliances typically include an elongate hollow body probe with proximal and distal ends and an inner lumen extending therebetween. For example, in an exemplary endoscope-type assembly, denoted generally as 200 in FIGS. 2A–2E, the probe is a hollow tube 208, incorporating such features. In an exemplary catheter-type assembly 300, shown in FIGS. 3A–3E, the probe is a hollow catheter sleeve 308 which incorporates such features. Assemblies 200 and 300 are described in greater detail later herein. At this point, it is to be noted that, in each of these embodiments, an extension member extends substantially the length of the probe (208 or 308), from the proximal to the distal probe end. A proximal end of the extension member is adapted to connect to linkage 36 of carriage assembly 32, for movement therewith. At its distal end, the extension member is adapted to mount a needle, as at 186 in FIGS. 2B and 3A, such that the needle will move with movement of the extension member. In this way, movement of carriage assembly 32 is transmitted to the needle, via linkage 36 and the extension member. Thus, when the carriage assembly is disposed at its retracted position, the needle likewise situates at a retracted position—typically within a distal-end region of the probe. When the carriage assembly is advanced to its extended position, the needle, too, will advance to an injection position—extending at least partially out of a distal-end region of the probe.

In the embodiment of FIGS. 1A–1E, linkage 36 is a relatively short, substantially rigid conduit. Here, linkage (conduit) 36 defines, in part, a fluid connection between reservoir 50 and a remote needle, such as described above. More particularly, linkage (conduit) 36 is adapted for fluid communication with reservoir 50 by way of a flow line 128 extending from the linkage (conduit), back up through a region of carriage assembly 32, and to an outlet of valve 118. Flow line 128 includes a flexible mid-region, e.g., formed of plastic tubing or the like, to accommodate the retracting and extending motions of the carriage assembly 32 that occur during acutation/deactuation. The forward end of linkage (conduit) 36 forms a fluid connection with the extension member. Here, the extension member is a hollow tube, as shown in part at 182 in FIG. 1E, having its proximal end received over the forward of the linkage (conduit 36) so as to form a fluid connection therewith, for transmitting fluid pressure from reservoir 50 to the needle.

In another embodiment, the extension member is a wire member operatively connected to the linkage at its forward end. The wire member is constructed of a material that is laterally flexible, permitting movement through tortuous pathways, and sufficiently incompressible along the longitudinal direction to provide for the efficient transmission of motion from the carriage assembly to the needle. Further in this embodiment, a fluid-carrying tube is provided for transmitting fluid pressure from reservoir 50 to the needle.

FIGS. 1F and 1G depict two alternative embodiments of a drug-delivery device, indicated generally as 100A and 100B, respectively, adapted for rapid deployment of a remote injection needle, as will now be described.

FIG. 1F shows an over-center-type delivery device mechanism to fire a piercing needle. As an actuator trigger 154 rotates between open and closed positions (in the direction shown by arrow "A"), an actuator cam, or pivoting member, 156 impinges on a follower 158 which meets resistance from two-condition leaf spring 160. The amount of force required to move follower 158 increases proportionally, as a function of the leaf spring, until an overcoming force is achieved. When the force reaches the predetermined amount, the leaf spring 160 flips, or "snaps," over center. The resultant rapid forward advance of drive rod 162, in direction "B," moves the carriage assembly 32 quickly forward—providing rapid deployment of associated drumg conduit and piercing needle assemblies (not shown).

FIG. 1G is a representative view of another embodiment of a spring loaded-type drug delivery mechanism of the delivery device of the present invention. In this additional embodiment, having particular utility in applications demanding rapid deployment of a drug conduit and piercing needle at a distal position, such as in MIS and catheter-type drug delivery, diagnostic and other procedures, actuator trigger 154 rotates as shown by arrow "A" causing cam 156 to impinge on follower 158. Follower 158 releases pawl 166, which pivots about pin 168 and rotates as shown by arrow "C," which allows spring 172 to "fire" guide rod 162 forward in direction "B." Spring-biased drive rod 162 is automatically retracted by tooth 174 in tooth housing 176 by spring 178, the spring 178 having a greater contractive force than the expansion force developed by spring 172.

Actuation of the delivery device of the invention can be manual, as shown, and can also be pneumatic, hydraulic, electronic, controlled by a microprocessor or externally. Attention is directed, for example, to the actuation means disclosed in co-pending U.S. patent applications Ser. No. 08/773,430 filed Dec. 27, 1996 and entitled "LASER DELIVERY MEANS ADAPTED FOR DRUG DELIVERY" by Murphy-Chutorian et al., Inc. and Ser. No. 08/773, 872 also filed Dec. 27, 1996 and entitled "LASER-ASSISTED DRUG DELIVERY" and by Murphy-Chutorian et al., which two disclosures are expressly hereby incorporated by reference.

In one embodiment, for example, one or both of the advancing means and compressing means includes electromechanical devices that can be electronically activated via an externally accessible electronic trigger, button or switch mounted on the device's housing. For example, with regard to the advancing means, a solenoid, stepper motor, worm screw, or other electro-mechanical device mounted within the device's housing can be actuated to advance a carriage assembly from a retracted position to an extended position, thereby effecting needle extension. Deactivation, then, can return the needle to its retracted position. The compressing means can also comprise any such electro-mechanical device. For example, a solenoid can be operatively connected to a plunger of a syringe barrel (reservoir) in the device's housing, for driving the plunger a selected distance along the barrel with each actuation.

Alternatively, one or both of the advancing means and compressing means can include hydraulic components, such as mechanically and/or electronically actuated piston/ cylinder assemblies operatively connected, e.g., via hydraulic fluid lines (e.g., liquid or gas), to respective plunger elements adapted for compressing the reservoir, and/or extending/retracting the carriage assembly.

Figure 8:
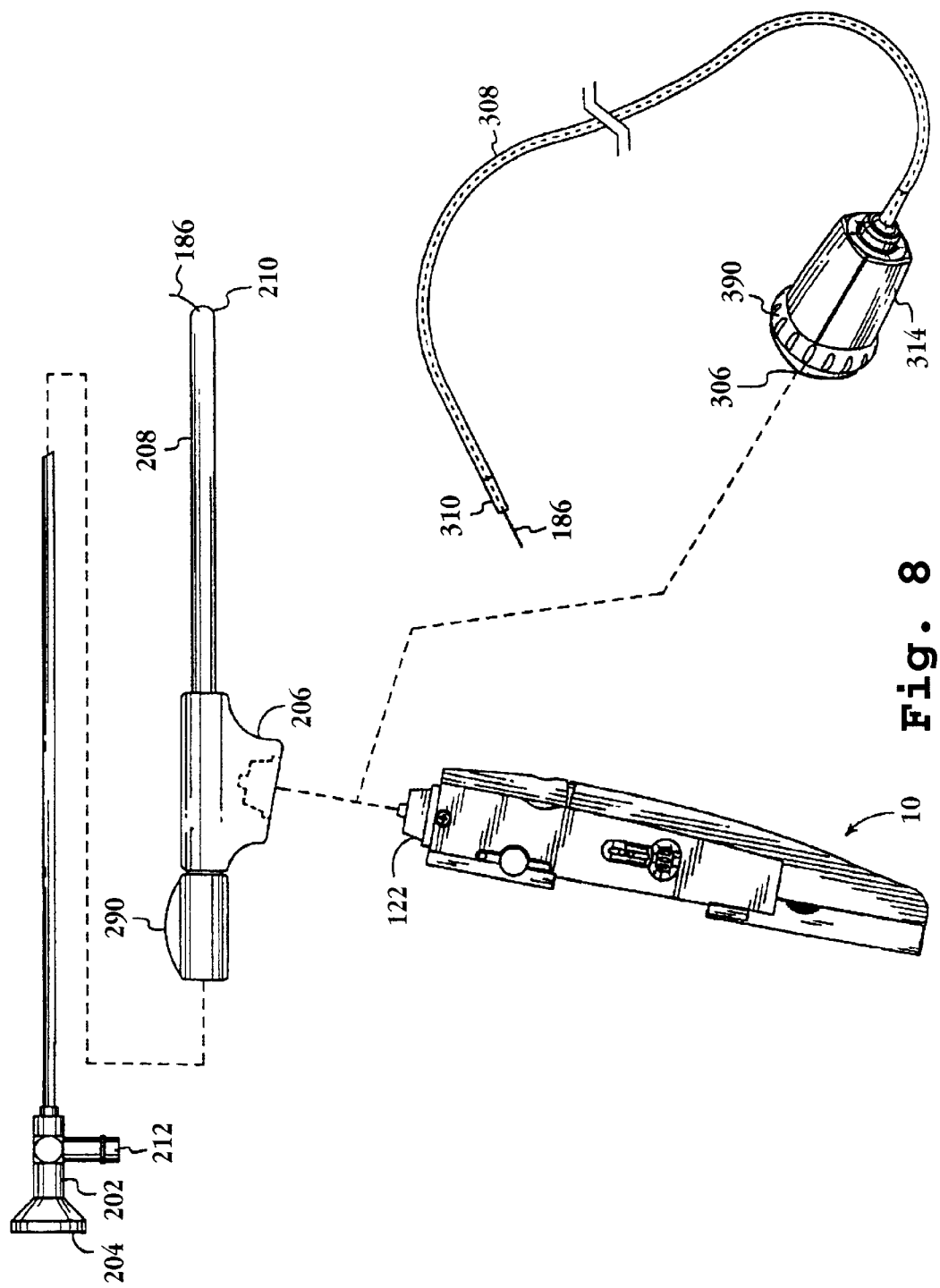
FIG. 8 is a representative schematic drawing of components of a drug delivery module kit of the present invention.

As mentioned above, the delivery device of the present invention is particularly well suited for use in connection with auxiliary equipment, such as catheters, endoscopes, etc. In this regard, an auxiliary equipment mount, such as at 122 in FIGS. 1A–1E, can be provided along a forward region of the device. Mount 122 is configured to bayonet or snap fit into associated endoscope or catheter portions (as best shown in FIG. 8) to position and secure the associated endoscope or catheter portions relative to the device. The mount can be any convenient means for coupling the device to other equipment, including a threaded portion, snap fit, clamps, etc. Furthermore, as will be described more fully herein, the device can be incorporated into a unitary endoscope or catheter or other type drug delivery device.

As previously mentioned, the reservoir of the delivery device (e.g., syringe barrel 50 of device 10 in FIGS. 1A–1E) can be employed to hold a therapeutic and/or diagnostic agent to be delivered. However, this will not always be desirable. For example, when the delivery device is used in connection with a medical appliance having an elongate hollow body probe, it would be necessary to pass the agent through the length of such probe in order to move it from a reservoir in the device housing to an injection needle at the distal end of the probe. Clearly, it would be advantageous to avoid such a long agent-travel path where expensive agents are being used e.g., rare proteins, etc. To this end, one embodiment of the invention provides the agent in a distal end of the appliance.

Figure 9A:
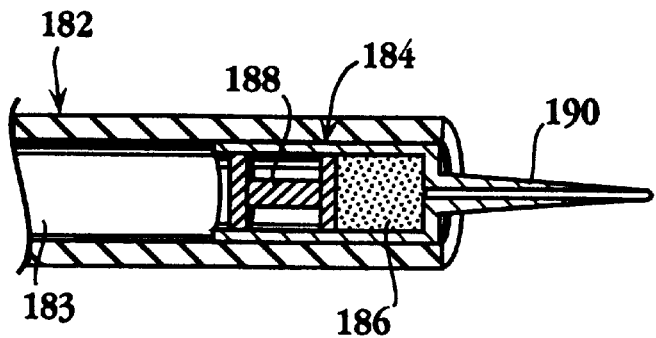
FIGS. 9A–9C show embodiments for providing an agent within a tube or container at a distal-end region of an elongate probe of a medical applicance, such as a catheter assembly.

In one particular embodiment, a micro-syringe device is provided at a distal end of an extension member that extends through an elongate hollow body probe of a medical appliance. In FIG. 9A, for example, the extension member is a hollow tube 182. A micro-syringe 184, containing a fluidic agent 186 therein (e.g., naked DNA) is inserted into a distal opening of the tube. The micro-syringe can be held therein by any suitable means, e.g., adhesives, frictional forces, heat sealing techniques, etc. Upon pressurizing a lumen 183 of tube 182 with a suitable gas or liquid, via the compressing means, a plunger element 188 of the micro-syringe can be pressed forwardly, so as to eject the agent through a needle 190.

Figure 9B:
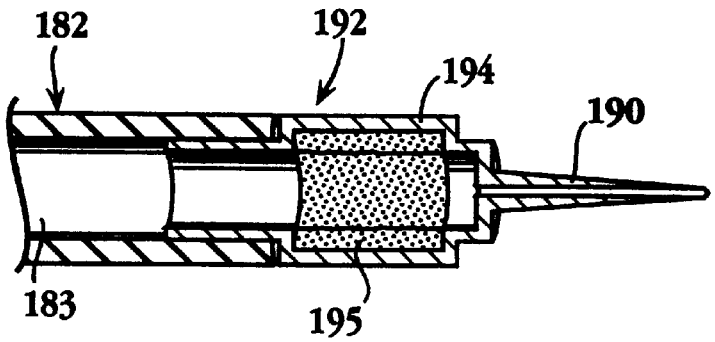
Figure 9C:
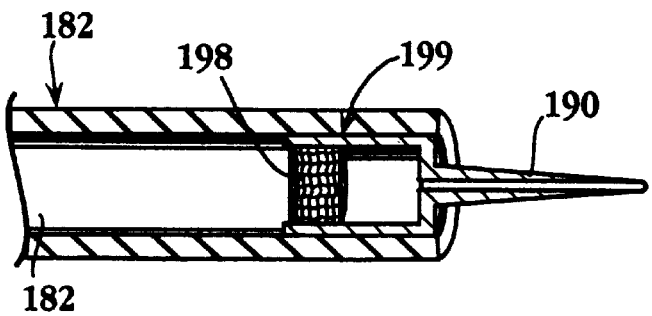

Certain other embodiments contemplate a drug container that can be inserted into a distal region of a tubular extension member. In FIG. 9B, for example, an insert 192 includes an expanded-diameter region 194 with a polymer matrix or other material (e.g., a filter paper-type material) 195 lining its interior sidewall. Prior to use, one or more selected agents can be precipitated or absorbed onto material 195. Upon passing a suitable solvent, or other appropriate fluid, into the tube so as to contact the agent-bearing material, the agent can be dissolved or otherwise pulled into the fluid and then delivered through needle 190. FIG. 9C shows a similar embodiment, except that the agent is precipitated or absorbed into a porous matrix or mesh material 198 extending across a passage of an insert 199.

Rigid Endoscope Type DDM for MIS and Other Surgical Applications

FIGS. 2A–2D are representative views of a modular or unitary endoscope-type drug delivery assembly 200 of the present invention. It will be understood that with respect to the cited advantage of providing a drug delivery device adaptable for use as a rigid endoscope-type device suitable for MIS or open surgical procedures, a central feature of the present invention is the drug delivery module (DDM). Thus, the unitary or modular assembly 200 enables a user to both extend a piercing needle and dispense drug or other agent or fluid therethrough, with a single, manual "draw" or squeeze force applied to an actuator (e.g., a trigger).

The drug delivery assembly 200 utilizes a rigid, viewing endoscope 202 with an eyepiece 204 at the proximal end held in an endoscope housing 206 which couples to the auxiliary mounting portion 122 of device 10. The present invention is for use with any of a wide variety of commercial, custom or other proprietary endoscopes or other visualization devices. The endoscope 202, for example, can be a 5.0 mm outside diameter standard or custom rigid endoscope, and about 300 mm in length. Such device can be used in conjunction with a 10.0 mm outside diameter tube 208. A smaller 2.0 mm endoscope can also be used with a smaller, such as a 6.0 mm outside diameter tube 208.

This endoscopic viewing assembly is similar to that used in other surgical instruments such as those disclosed in co-pending U.S. patent application Ser. No. 09/031,752 filed Feb. 27, 1998 and entitled "VIEWING SURGICAL SCOPE FOR MINIMALLY INVASIVE PROCEDURES" by Daniel et al., which is hereby incorporated by reference.

The endoscope assembly 200 has a generally rigid distal, elongated hollow tube portion 208 and a distal tip 210. It will be understood, and become more apparent by the following, that the elongated hollow tube portion 208 comprises a single or multi-lumen shaft for containing an extension member, drug delivery channel, optional visualization, etc. It will be understood that endoscope port 212 is typically used as an access for providing a light source at the target viewing area, such as via fiber optic cable, bundle, etc. (not shown). Thus, the inside diameter of endoscope portion 208 which can be used is largely a function and dependent on the outside diameter of the rigid endoscope 202 selected for use with the assembly 200 of the present invention.

A hollow tube-type drug conduit 282 extends from the mount portion housing 206 through the elongated portion 208 of the endoscope assembly 200 and terminates in an extendable, piercing needle 186. The entire drug conduit 282 slides inside a lumen of the elongated portion 208 and couples to the connector tube 182 between the auxiliary equipment mounting portion 122 of the device 10 and the mount housing portion 206, such that when the connector tube 182 of the device 10 is advanced and retracted, the piercing needle 186 is co-extensively advanced and retracted.

Drug or other fluid flows from syringe reservoir 50 in device 10 through flow line 128 and connector 182 into drug conduit 282 when the device 10 is actuated. The distal tip 210 of elongated tubular portion 208 can be oriented by scope adjustment knob 290.

As shown, the ergonomic shape of the endoscope assembly 200 provides for a plurality of orientations for the assembly 200 in operation, including using a pistol-grip on the device 10, gripping the forward, endoscope mount portion 206, or the assembly 200 can be supported such that the device 10 extends above the endoscope device 200 and the endoscope mount portion 206.

It will be understood that, while in a modular assembly in which the device 10 is used with the endoscope portions, as described with reference to FIGS. 2A–2D, the actuation trigger is located on the device itself, and that the needle activation trigger may be positioned on the scope portion or other housing portion as desired, resulting in similar action of the needle and drug or other agent dosing function. These embodiments will be considered within the scope of the present invention. The trigger can be moved to any other part of the assembly, however, including to the mounting housing 206, etc., as will be apparent to those skilled in the art, and the functions of the device 10 and associated assembly would be essentially identical to as described herein.

As shown in FIG. 2E, yet another preferred embodiment of an endoscope-type drug delivery assembly 200A with device 10 of the present invention has an articulating portion. Pivot connection 209 allows rotational movement between the endoscope 202 and the endoscope mount portion 207, thus allowing selection of functional angle Θ. In operation, a surgeon or cardiologist will find the controllability and selectability of functional angle Θ a feature which increases efficiency, ease of operation and adaptability to specialized or general applications. Selection of functional angle Θ is based on the intended application, however, it will be understood that an angle between about 45 degrees and about 135 degrees, or more or less, is typically used.

It will be understood that the embodiment shown in FIG. 2E will have a locking mechanism, to prevent undesirable, or to perform advantageous, motion of the device 10 relative to the rigid scope portions of the assembly 200A. Such locking mechanism could be ratcheted, or otherwise indexed, continuously adjustable, comprising interlocking teeth, compressible components secured by threadably engaging portions or otherwise, or have a spring activated, retracting pin engageable within one or more engagement slots located radially or otherwise on an opposing member, etc. as described, the locking mechanism could be implemented in numerous ways, and safety and efficacy considerations would be key.

Elongated, Flexible Catheter Type DDM for Percutaneous and Other Trans-Luminal Applications FIGS. 3A–3E are representative views of a modular or unitary catheter-type drug delivery assembly 300 incorporating the delivery device 10 of the present invention. Again, as with the endoscope-type DDM assembly of FIG. 2A et seq., the unitary or modular assembly 300 enables a user to both extend a piercing needle and dispense drug or other agent therethrough, with a single, manual "draw" or squeeze force applied to a trigger.

This steerable catheter assembly is similar to that used in other percutaneous instruments such as those disclosed in co-pending U.S. patent application Ser. No. 08/833,352 filed Apr. 4, 1997 and entitled "STEERABLE CATHETER" by Giba et al., which is hereby incorporated by reference.

The elongated portion 308 of the assembly 300 comprises a single or multi-lumen flexible sleeve or shaft for containing at least one drug delivery channel in a drug delivery tube 382, with optional visualization, etc. It will be understood that assembly 300 provides, optionally, a light source at the target viewing area, such as via fiber optic cable, bundle, etc.

The delivery device 10 is configured to bayonet or snap fit into the lower extremity of the catheter mount 306 which locks onto the auxiliary equipment mounting portion 122 of the device 10.

The connector tube 182 extends through the catheter mount 306 and is sealed to drug conduit 382. Drug conduit 382 extends through elongated tubular portion 308 of the catheter assembly 300 to the distal tip 310 of the elongated portion 308 where the drug conduit 382 connects to the piercing needle 186.

It will be understood that elongated shaft portion 308 may comprise a single lumen or multi-lumen extrusion. In a preferred embodiment, an inner lumen 309 extends coextensively and/or coaxially with the elongated shaft portion 308 and physically separates control wire 330, etc., from drug conduit 382. Thus, the mechanical steering mechanism is physically separated from the drug conduit 382, thus minimizing the risk of contamination of the drug, fouling of the internal passages or other failure of the steering mechanism, etc.

Thus, flow of liquid, solid or vapor phase drug, solution or other agent or compound is communicated from the reservoir in the device 10 through drug conduit 382 and is dispensed through piercing needle 186 subsequent to advance of piercing needle 186 through the distal tip 310 of assembly 300. The distal tip 310 of elongated tubular portion 308 of catheter assembly 300 can be oriented by steering adjustment finger control knob 390, as will now be discussed.

Figure 3C:
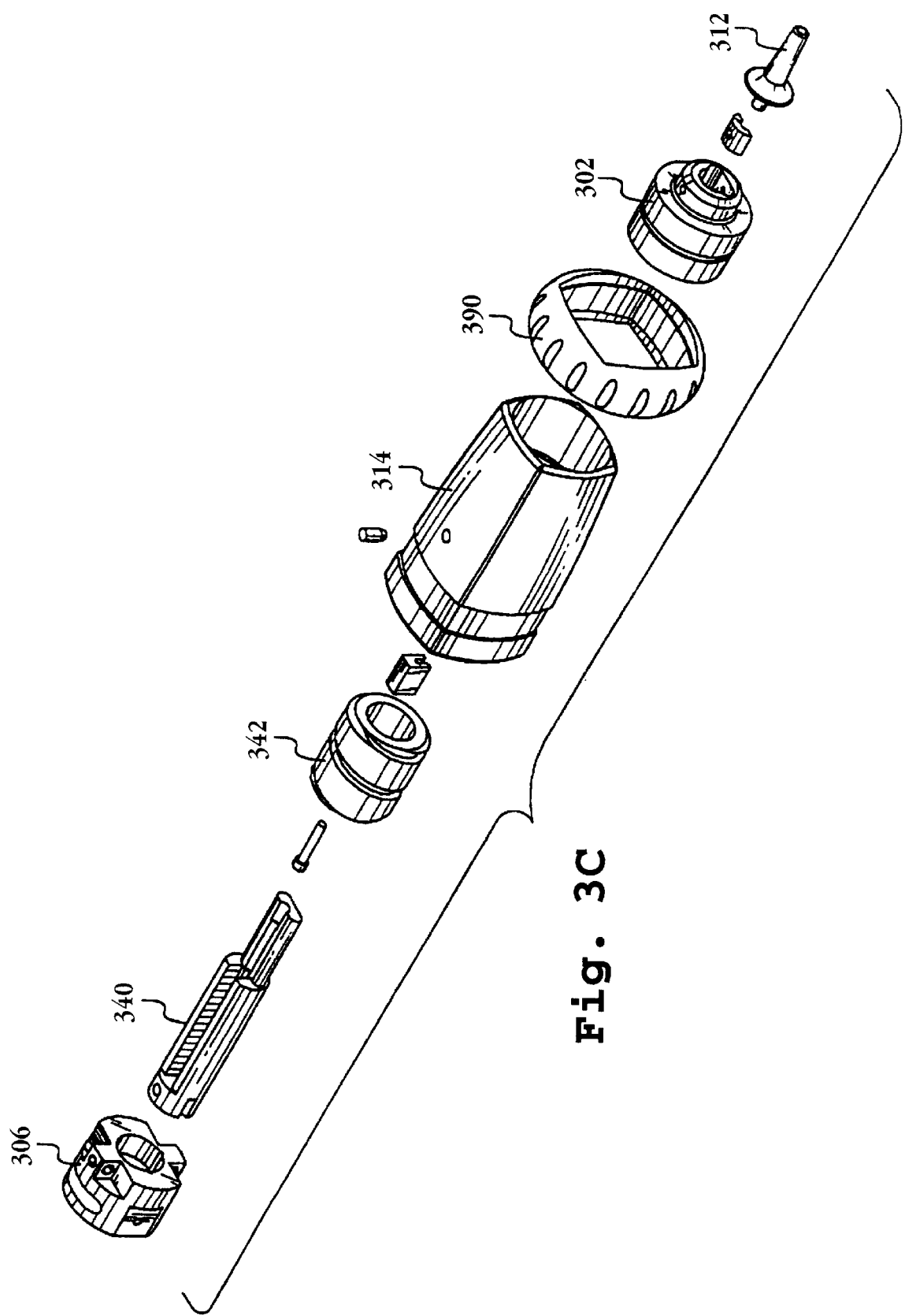
FIG. 3C is a representative partial separated view of a control portion of a modular or unitary catheter-type drug delivery device of the present invention.
Figure 3D:
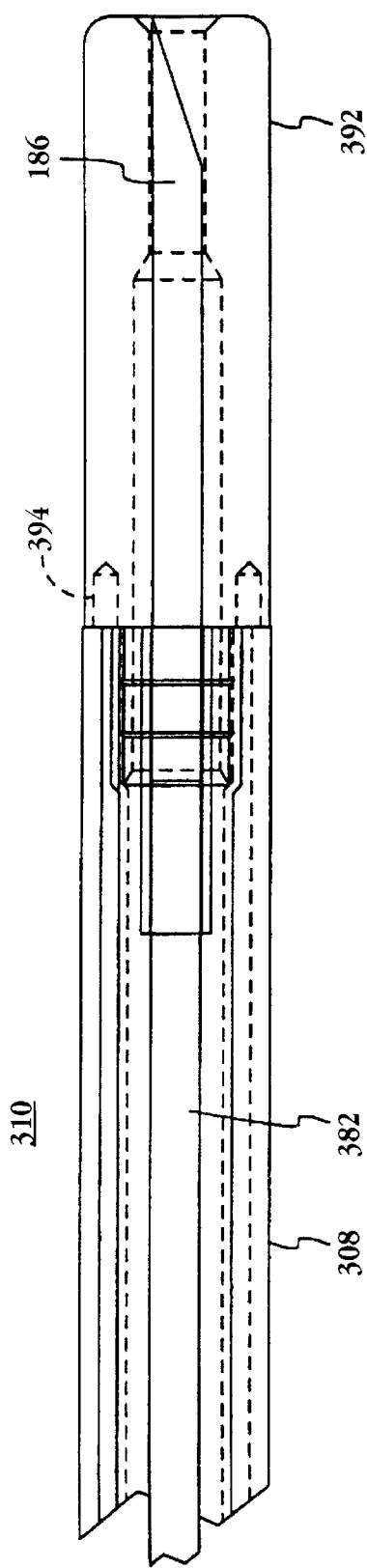
FIG. 3D is a representative partial section view of the distal end portion of a modular or unitary catheter-type drug delivery device of the present invention.
Figure 3E:
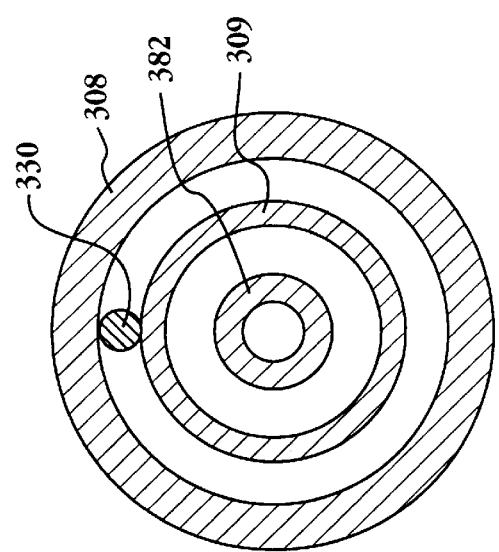
FIG. 3E is a representative cross-section view of the elongated portion of a modular or unitary catheter-type druig delivery device of the present invention.

The assembly of the catheter portion is shown in FIG. 3C. Catheter cap 302 is the attaching member for the exterior portion of the elongated steerable catheter sheath 308, strain relief 312 and steering housing 314. Within the catheter cap 302, set screw 316 fixes the assembly to the elongated catheter sheath 308. Set screw 318 fixes leadscrew guide 340 axially through the annular opening through leadscrew 342, maintaining the assembly integrally.

The steering housing 314 allows insertion of leadscrew 342, which is then captured and retained in place when the catheter mount and coupling 306 is installed. Leadscrew has external threads with a pitch corresponding to about 2 revolutions per inch of linear travel. In a completed assembly, leadscrew 342 can be moved in a linear fashion to articulate the distal tip 310 of the steerable catheter device 300 by rotation of finger control knob 390 situated on the exterior of steerable housing 314.

Articulation of the steerable catheter tip 310 is accomplished by push-pull forces on cable 330 extending between distal tip 310 and leadscrew 342, coextensive and/or coaxial with steerable catheter sheath 308. The cable 330 is press fit at the interface of key 322, which secures the cable 330 and prohibits the advancing bushing 320 from rotating within the steering housing 314 when a linear motion is applied. When the finger control knob 390 is rotated with steering housing 314, articulation of the attached steerable catheter tip 310 can be achieved. Thus, the catheter tip 310 can be guided through the vasculature, through other body lumens, into a body organ or other structure. Upon determining a proper target location, the needle 186 can be advanced and the desired dose of the prescribed drug agent can be released by actuating delivery device 10. At the distal tip 3 10, elongated catheter sheath 308 couples to protective tip portion 392.

Thus, it will be apparent to those skilled in the art, based on the foregoing, that the steerable components of the catheter-type drug delivery assembly 300 is but one choice of catheter assembly. It will be apparent to those skilled in the art that the steerable catheter device 300 is but one example of a catheter having a lumen and an exit port at a distal end, and other known catheter systems may be adapted for use with the device 10 of the present invention.

Piercing Needle Advance and Drug Delivery At Distal End

Figure 4A:
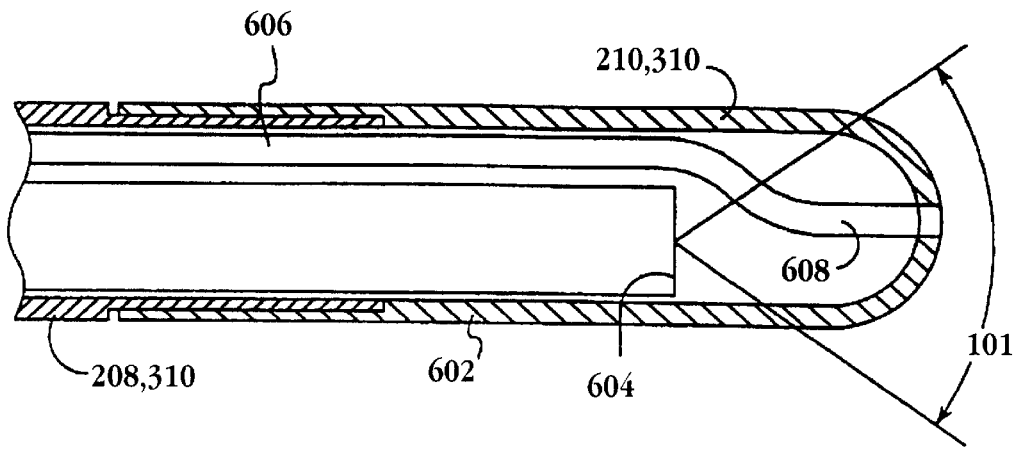
FIGS. 4A–4D are representative section views of tubular viewing assemblies of the drug delivery devices of the present invention having clear distal tipped sections with a working channel, and having various orientations at the clear distal tip.
Figure 4B:
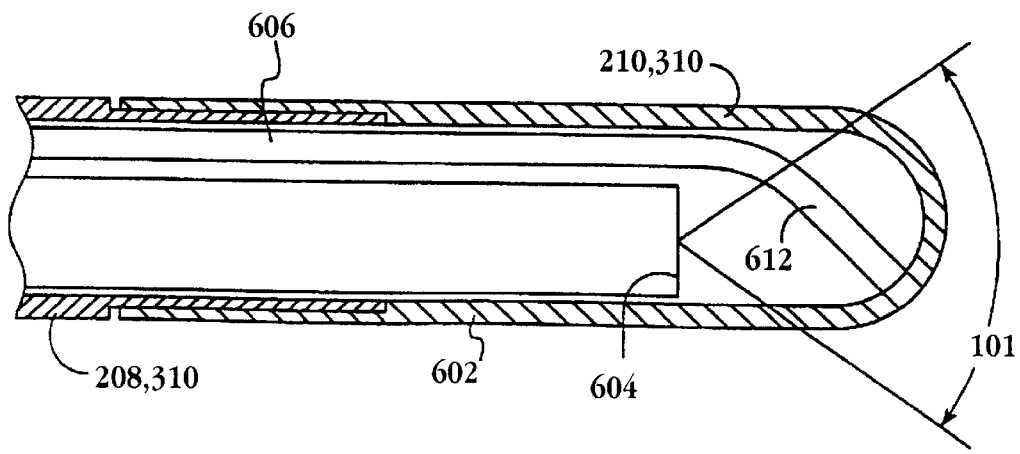
Figure 4C:
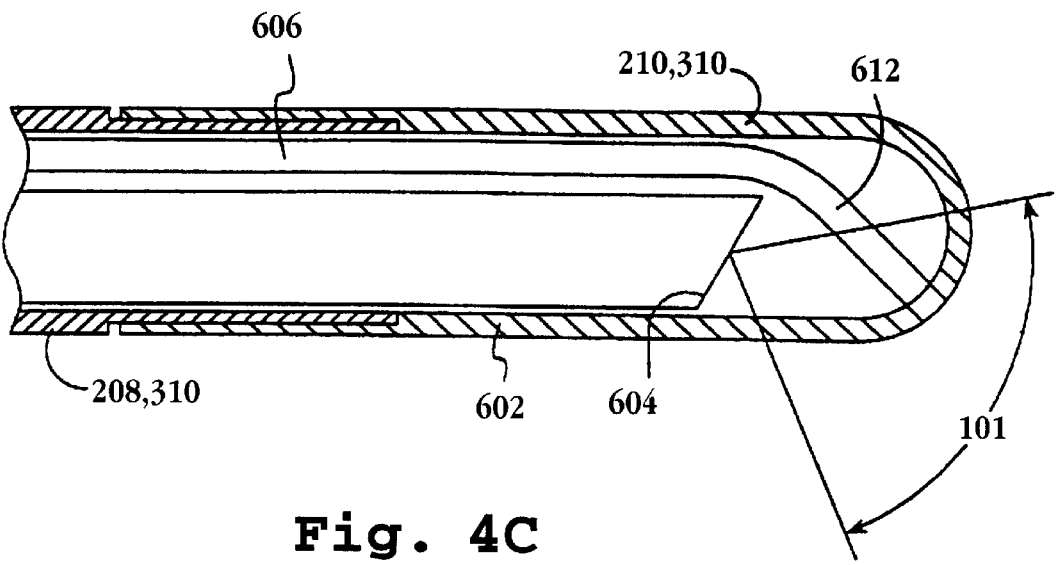
Figure 4D:
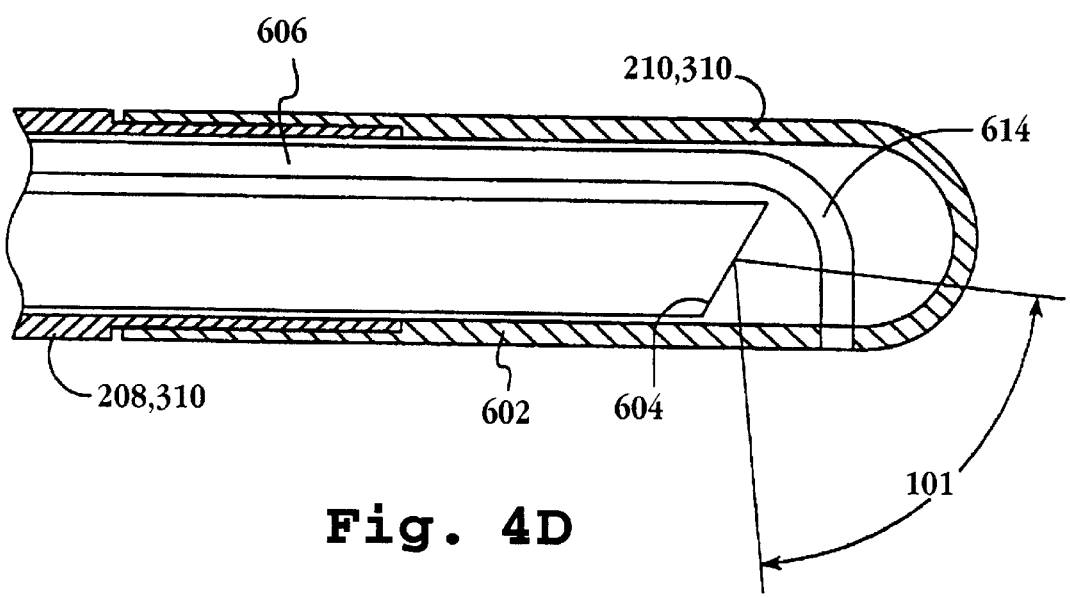

FIGS. 4A–4D are representative section views of tubular viewing assemblies of the delivery devices of the present invention having clear distal tipped sections with a working channel, and having various orientations at the clear distal tip. The assembly has an optically clear or transparent end tube cap 602 which fits over the visualization port distal end 604 of a scope's visualization shaft and has a working channel 606 for communication of the drug or other material fluid, solution, solid or vapor to the target region. It will be understood that the distal ends 604 in FIGS. 4A & 4B lie in planes essentially perpendicular to the central axis of what would be the elongated portions 208 or 308 of the devices 200 or 300, respectively, such that optics provide essentially direct forward visualization with a predetermined divergence viewing angle Φ as shown. In contrast, the end ports 604 shown in FIGS. 4C & 4D are at a 30° angle with respect to what would be the central axes of the elongated portions 208 or 308 of the assemblies 200 or 300, respectively. Distal ends 604 can be varied such that the field of view is at an angle offset with respect to the central axis of elongated portion 208 or 308 of the devices 200 or 300, respectively.

The end cap 602 members are made from an acrylic polycarbonate or other transparent material and coupled to the elongated portion 208 or 308 of the assemblies 200 or 300, respectively. The distal end of the visualization scope 604 terminates near the transparent end cap 602. The end caps 602 can be made with desired optical light absorption/reflection characteristics. Furthermore, the shape of the end cap 602 can be conical, elliptical or include planar facets at various angles with respect to the central axis of the elongated portion 208 or 308 of the devices 200 or 300, respectively. The end caps 602 are designed and made in accordance with required optical lens characteristics including but not limited to focus, divergence, convergence, directionability, collimation, polarization or diffusion.

The working channels 606 have various designs with differilg bends that cooperatively are attached to the distal ends 600. The working channels 606 as shown are internal to the assemblies 600, but can be incorporated into an external lumen or be defined by a structural tube either in the wall of the tip assembly 600 or conformably designed to fit within the inner wall surface of assembly 600 along with the distal end 604 of the visualization scope or an end shaft of an endoscope. The working channel 606 is shown attached to the internal wall of assembly 600 in FIGS. 4A–4D. Tip assembly 600 functions to allow visualization of diagnostic or affected tissue while placing the tip in contact with the target tissue, optionally applying pressure to tissue thereby stopping any bleeding and minimizing active tissue movement, e.g. a beating heart.

The working channel 606 directs and protects the operative piercing needle (not shown). The working channel 606 can be made of stainless steel, plastic or comparable material. The working channel 606 in FIG. 4A has a curvature 608 such that the piercing drug delivery needle or other working device is directed through the transparent end cap 602 in a direction essentially parallel with or contiguous with respect to the central axis of the associated elongated sheath portion. In FIGS. 4B & 4C, the working channel 606 has a curvature 612 which directs the drug delivery piercing needle or other working device through the transparent end cap 602 at approximately 45° with respect to the central axis of the elongated portion. Likewise, the curvature 614 in the working channel 606 of FIG. 4D directs the drug delivery piercing needle or other working device through the transparent end cap 602 in a direction approximately 900 with respect to the central axis of the elongated endoscope or catheter portion. Other orientations of working channel 606 and/or distal end bends in tube 606 can be used to direct a working device.

Figure 2A:
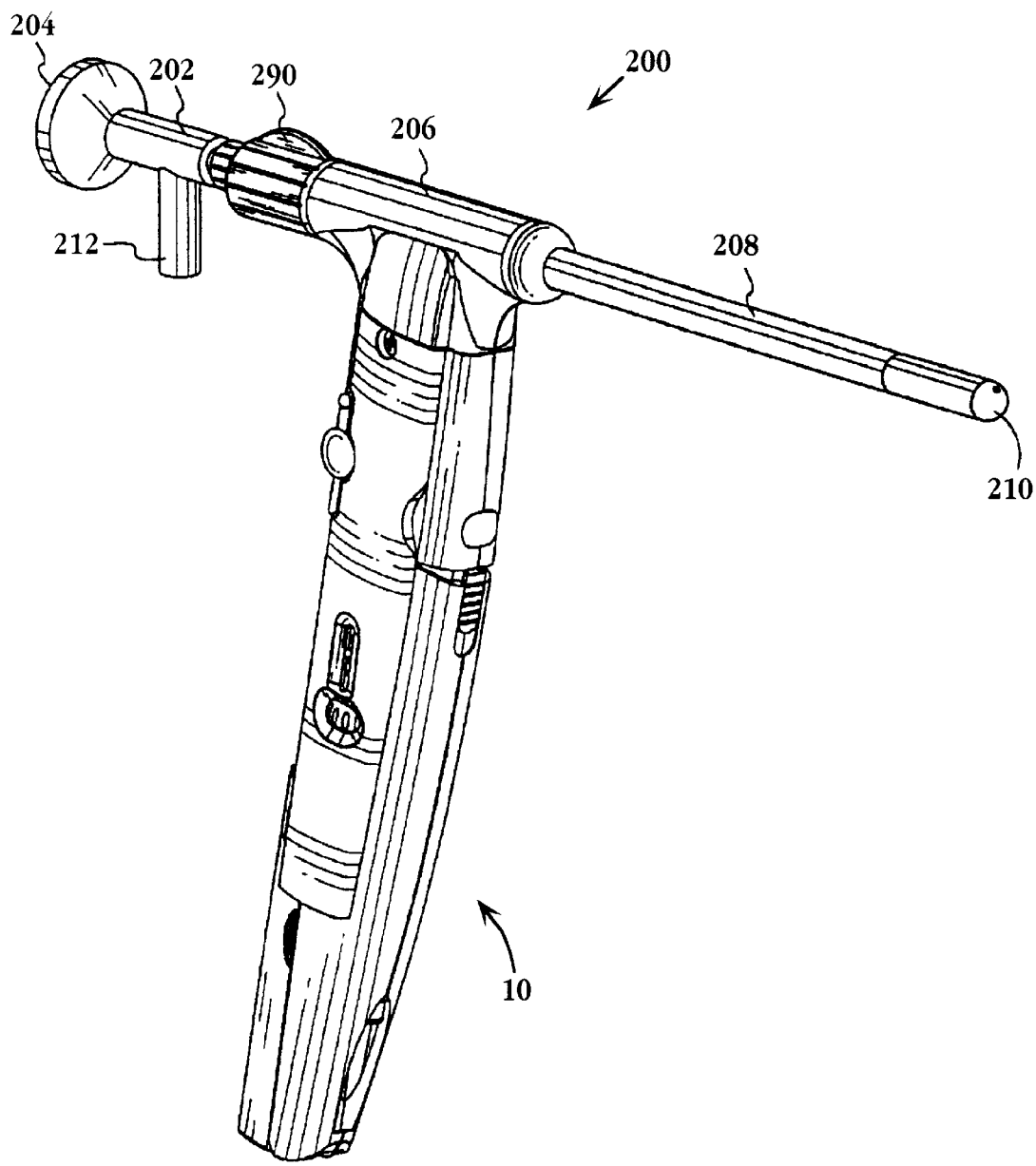
FIG. 2A is a representative isometric view of a modular or unitary endoscope-type drug delivery device of the present invention.
Figure 2C:
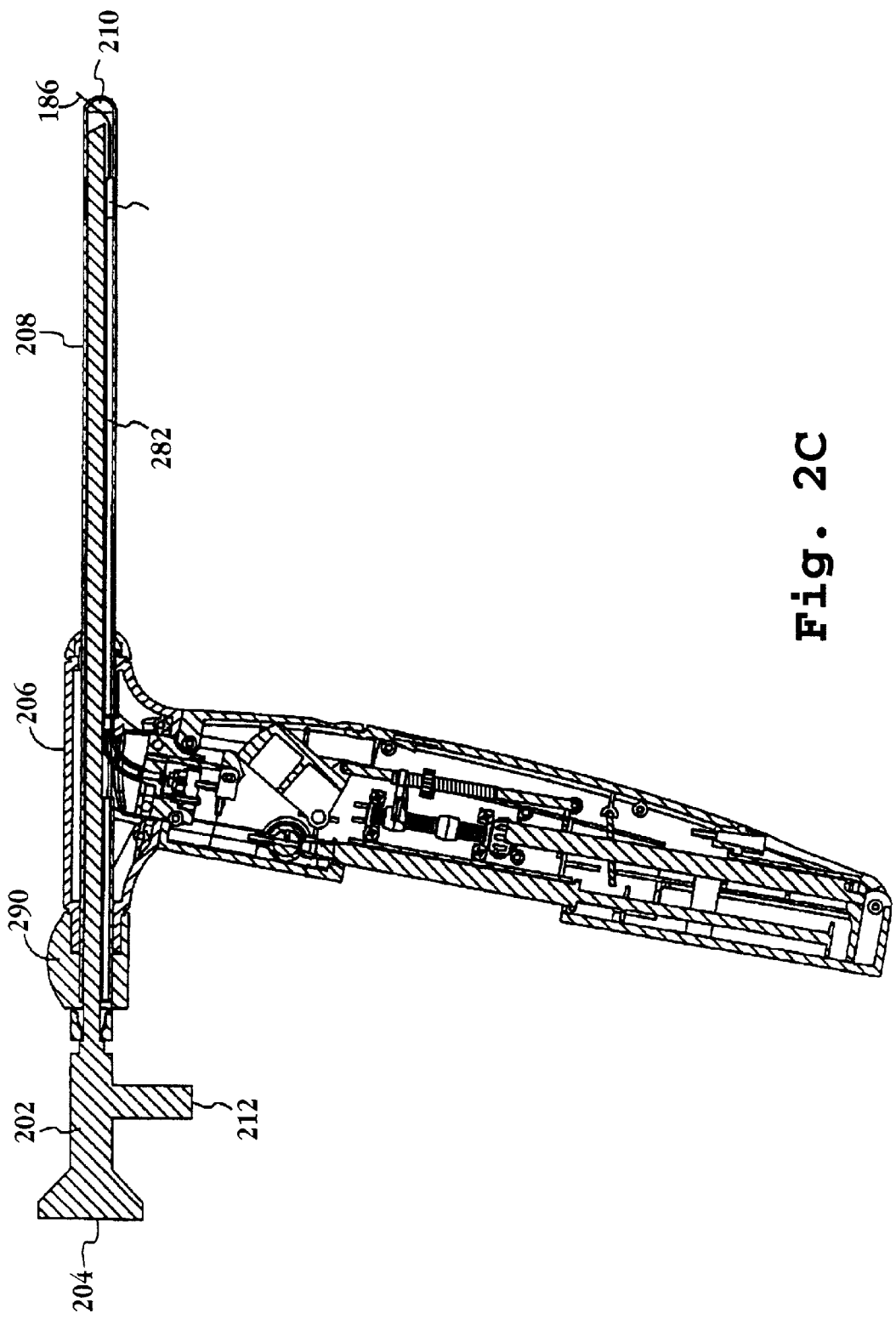
FIG. 2C is an internal view of a modular or unitary endoscope-type drug delivery device of the present invention.
Figure 2D:
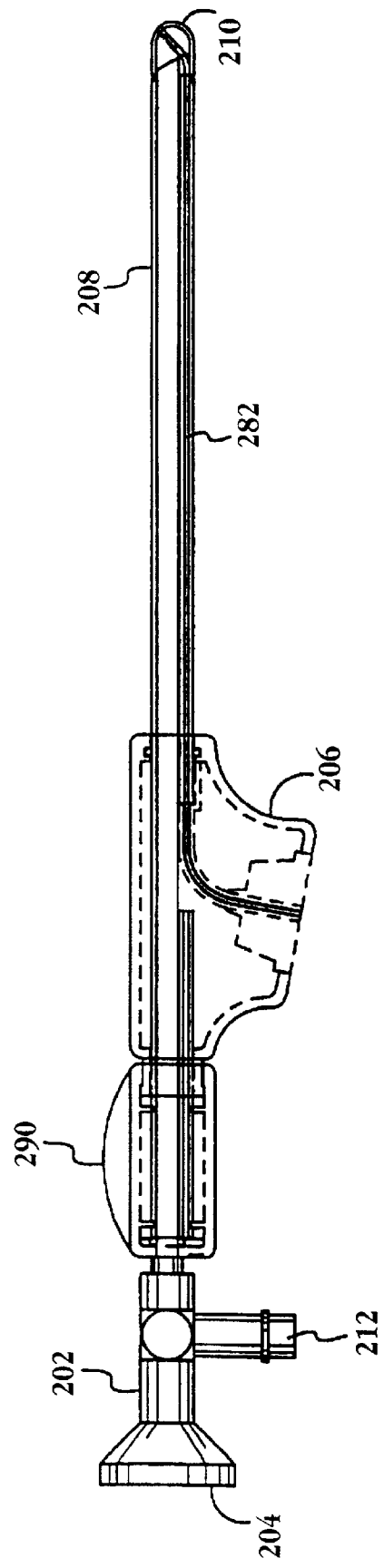
FIG. 2D is a partial view of a modular or unitary endoscope-type drug delivery device of the present invention.

It will be understood that this tubular assembly may be placed over a conventional endoscope or may be incorporated at the distal end of the unitary or modular MIS device shown in FIG. 2A, or used at the distal end of a catheter assembly.

FIGS. 5A & 5B are representative views of a flexible piercing needle 186 located at the distal end of the elongated, tubular shaft portions 208 (in the endoscope-type drug delivery assembly 200) and 308 (in the catheter-type assemblies 300) of the present invention. Piercing needle end portion 702 has a bevel cut end tip 704 or other operable tip for piercing tissue and delivering drug or other compound therethrough.

Between rigid piercing distal end portion 702 and the remainder of drug conduit 282 and 382, an intermediary flexible coupling portion 708 allows a degree of flexibility between the distal end portion 702 and the drug conduit 282 and 382 portion of piercing needle 186. This combination construction allows passage of the piercing needle 186 through a working channel (such as indicated by reference numeral 606 of FIGS. 4A–4D) with bends and curves. As shown in FIG. 5A, the flexible coupling 708 comprises an integral section of flex tubing, and as shown in FIG. 5B, the flexible coupling 708 comprises a spliced section of flexible tubing, such as silicone, rubber, or comparable material.

The drug conduits 282 or 382 of the present invention are manufactured using high quality, specialized materials and methods of construction. A preferred embodiment is manufactured by Putnam Precision Molding, Inc. of Putnam, Connecticut. The tubing has an inside diameter of about 30 mils and an outside diameter of about 43 mils. The co-extrusion comprising stainless steel wound nylon tubing provides high columnar strength to prevent against failure of the drug conduit 282 or 382 in high flex situations such as articulation of the distal tip of a catheter device, extension of the piercing needle through small radius of curvature bends, etc.

FIG. 5C is a representative section view of a distal end portion of a drug delivery device of the present invention. The tubular wall 720 of the rigid endoscope or elongated catheter shaft coupled to the device 10 (not shown) of the present invention has at least one lumen 722 for the drug conduit (such as 282 and 382, above) to pass through protected. Another lumen 724 is adapted to receive a visualization device including an endoscope or other fiber optic device. Shaped lumen 726 is oriented adjacent the tubular wall 720 to act as a guide channel for a steering wire, push rod or other control mechanism.

FIG. 6A is a representative internal view of a tubular viewing assembly having a controllable distal tip. In this embodiment, and also as shown in FIGS. 4A–4D with respect to either or both the endoscope-type embodiments as well as the catheter-type assemblies, the elongated, tubular shaft portions 208 (in the endoscope-type drug delivery assembly 200) and 308 (in the catheter-type assemblies 300 of the present invention) contain one or more lumens, the lumens optionally containing a visualization scope 604 or other operative device. An advanceable drug conduit 282 (in the endoscope-type drug delivery assembly 200) and 382 (in the catheter-type assemblies 300 of the present invention) lies within a controllable working channel 706. The working channel may also be excluded in optional embodiments, in which case the drug conduit itself, as described herein, would lie within or outside of the elongated portion 208 (in the endoscope-type drug delivery assembly 200) or 308 (in the catheter-type assemblies 300 of the auxiliary associated equipment of the device 10 of the present invention.

It will be understood, therefore, that drug conduit 282 (in the endoscope-type drug delivery assembly 200) and 382 (in the catheter-type assemblies 300 of the present invention) terminating in piercing needle 186 passes through the controllable working channel 706. Piercing needle 186 comprises a sharpened distal tip portion 702 and is advanceable through septum member 603. The precise position at which the piercing distal tip 702 pierces the septum portion 603 is determined by the axial motion of guiding member 605 acting on controllable working channel 706. Thus, the angle of advancement of the distal tip 702 of piercing needle 186 is determined by the orientation of guiding member 605 through which piercing tip 702 passes, as selectively and controllably oriented by control shaft 607 moved according to arrow "D." Guiding member 605 pivots about pin 709 and is linked to control shaft 607 at pin 611. Guiding member 605 is mounted within the distal tip portion of the viewing assembly, housing assembly, etc.

FIG. 6B is another representative internal view of a tubular viewing assembly having a controllable distal tip. As described above, drug conduit 282 (in the endoscope-type drug delivery assembly 200) and 382 (in the catheter-type assemblies 300 of the present invention) terminating in piercing needle 186 passes through the controllable working channel 706 and is advanceable through septum member 603. In this embodiment, however, the relative radial positions of control shaft 607 and drug delivery piercing needle tip 702 are transposed. In either case, the position at which the piercing distal tip 702 pierces the septum portion 603 as well as the direction at which it pierces, penetrates or otherwise extends to the outer surface of the septum 603 or beyond and into target tissue or to a target region for delivery therein, therethrough or thereabouts, and at which angle relative to the central axis of the elongated tubular portion of the device as also indicated by direction arrow "D," is determined by guiding member 605. As mentioned above, the elongated portions 208 and 308 have either a single, tubular lumen region or have a plurality of lumens, formed such as by extrusion (see FIG. 5C).

Method of Use

Figure 7A:
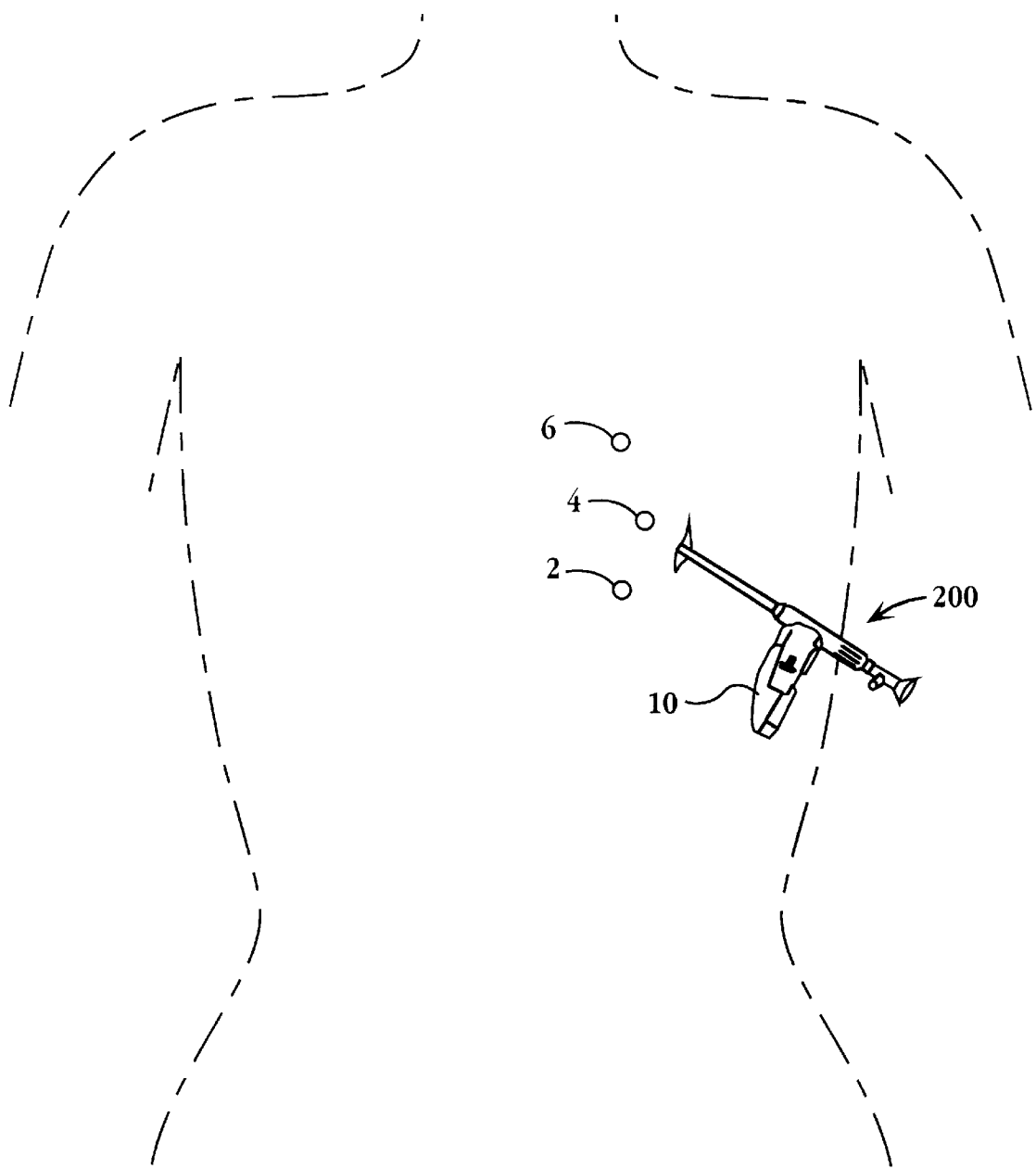
FIG. 7A is a perspective view of a patient, showing a method of use of the endoscope-type device of the present invention.

FIG. 7A is a perspective view of a patient, showing a method of use of the endoscope-type device of the present invention. It will be understood that the example given in this drawing is an MIS application, and that the device 10 of the present invention may also be used in conjunction with surgical procedures.

The perspective view of a patient shows first, second and third minimally invasively formed penetrations in a patient's chest, 2, 4 and 6, respectively. It will be appreciated that the exact location of penetrations 2, 4 and 6 is not limited to those shown. Additionally, from 1 to N+1 numbers of penetrations may be made. The patient is prepared for the procedure and is positioned similarly to that used for a left thoracotomy. The patient's left arm is draped. A conventional double lumen endotracheal tube is used to selectively deflate one side or the other of the lungs. Preferably the left lung is collapsed which allows access to the chest cavity in the vicinity of the left lung. The other lung remains inflated to provide oxygenation.

With regard in particular to cardiac procedures, the distal tip of surgical drug delivery device 200 is positioned to reach a desired aspect of a ventricular wall. A distal portion of the drug delivery device 200 is positioned against tissue of the wall of the heart. The visualization features of the drug delivery device 200 can be used to visualize the area, look for larger coronary vessels, to inspect the condition of the pericardium, and to check for adhesions. The shape of the heart as well as its position is visualized.

The endoscope or other interventional device 200 can include a CCD camera device attached to the eyepiece for viewing on a monitor. Additionally, additional viewing scope devices can be used during the procedure as inserted in the first penetration and the rigid scope can be inserted into second penetration 4.

The drug delivery conduit with piercing needle is inserted through the working channel of the device 200 (such as indicated by reference numeral 722 in FIG. 5C, by 606 in FIGS. 4A–4D and by 706 in FIGS. 6A and 6B). Once the desired number of drug delivery tissue sites have been treated, the device 200 can be emplaced in any of the other penetrations. It will be recognized that the procedure will vary, depending on a particular surgical requirement. For instance, drug delivery may be performed prior to, during or after other cardiac procedures, such as CABG and TMR.

Figure 7B:
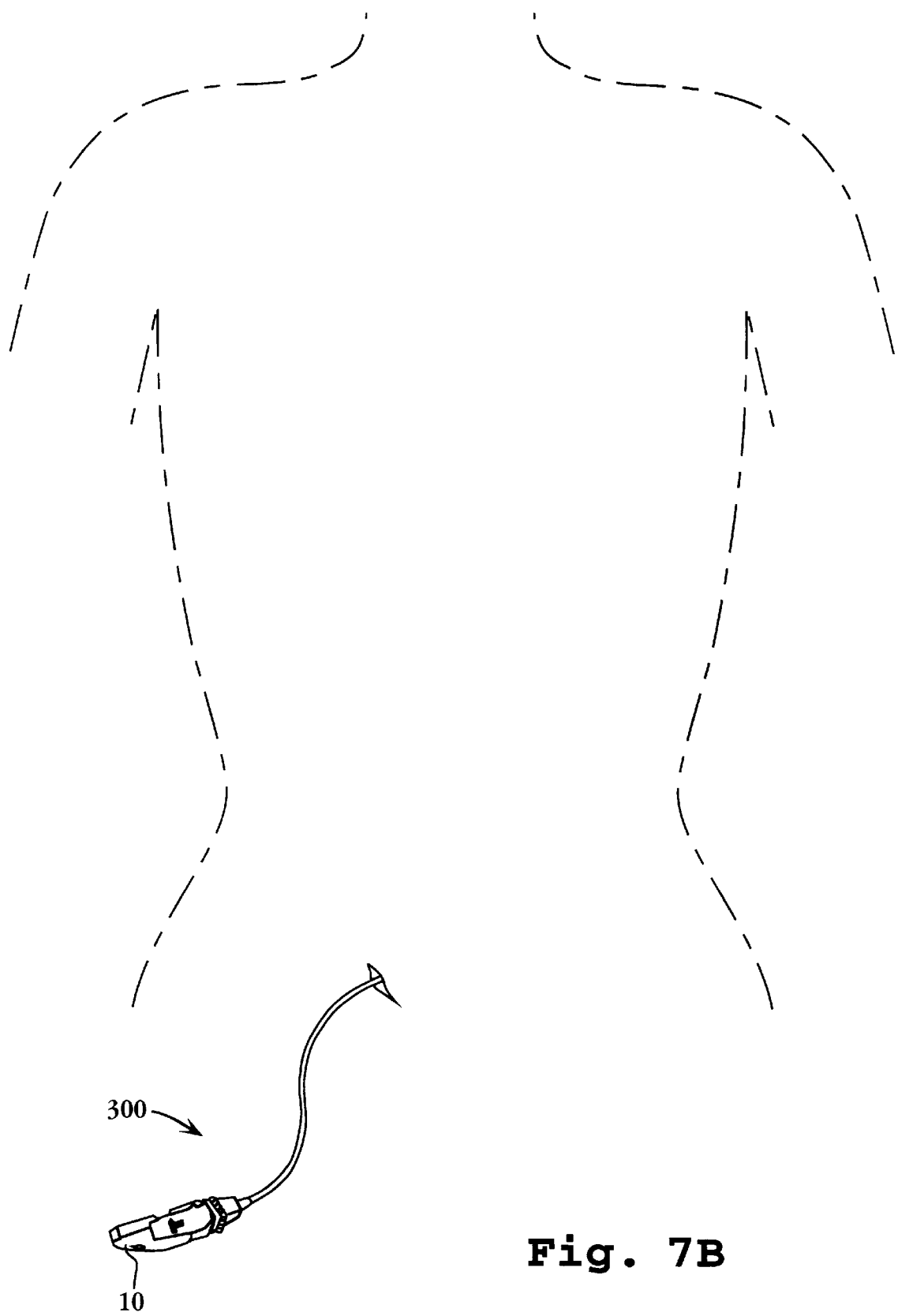
FIG. 7B is a perspective view of a patient, showing a method of use of the catheter-type device of the present invention.

FIG. 7B is a perspective view of a patient, showing a method of use of the catheter-type device of the present invention. When the interventional procedure involves using the percutaneous catheter-type delivery assembly 300, the assembly 300 is positionable adjacent the coronary ostia, within the coronary arteries themselves, inside, beyond or elsewhere with relationship to the various valves and chambers of the heart as well as near any portion of the heart's endocardial surfaces for drug treatment. As described above, drugs can be delivered to tissue via advanceable drug conduits with piercing needle tips which pass through a working channel of the instrument. The catheter-type assembly 300 can, in preferred embodiments of the methods of the present invention, be inserted through the femoral artery in the groin region and passed into the heart over the aortic arch and, optionally, into the left ventricle. Treatment sites within the ventricles typically require a catheter having a length of up to 120 cm. Percutaneous drug delivery can be achieved using the drug delivery assembly 300 with delivery device 10 of the present invention.

Other surgical and/or percutaneous or transluminal procedures in which the devices of the present invention are particularly adapted include delivery of drug or other agents within the gall bladder, tumors or other structures, or in laparoscopy or laparotomy, colosectomy and other MIS operations in which auxiliary, working devices for treatment of diseased tissue are used.

Figure 7C:
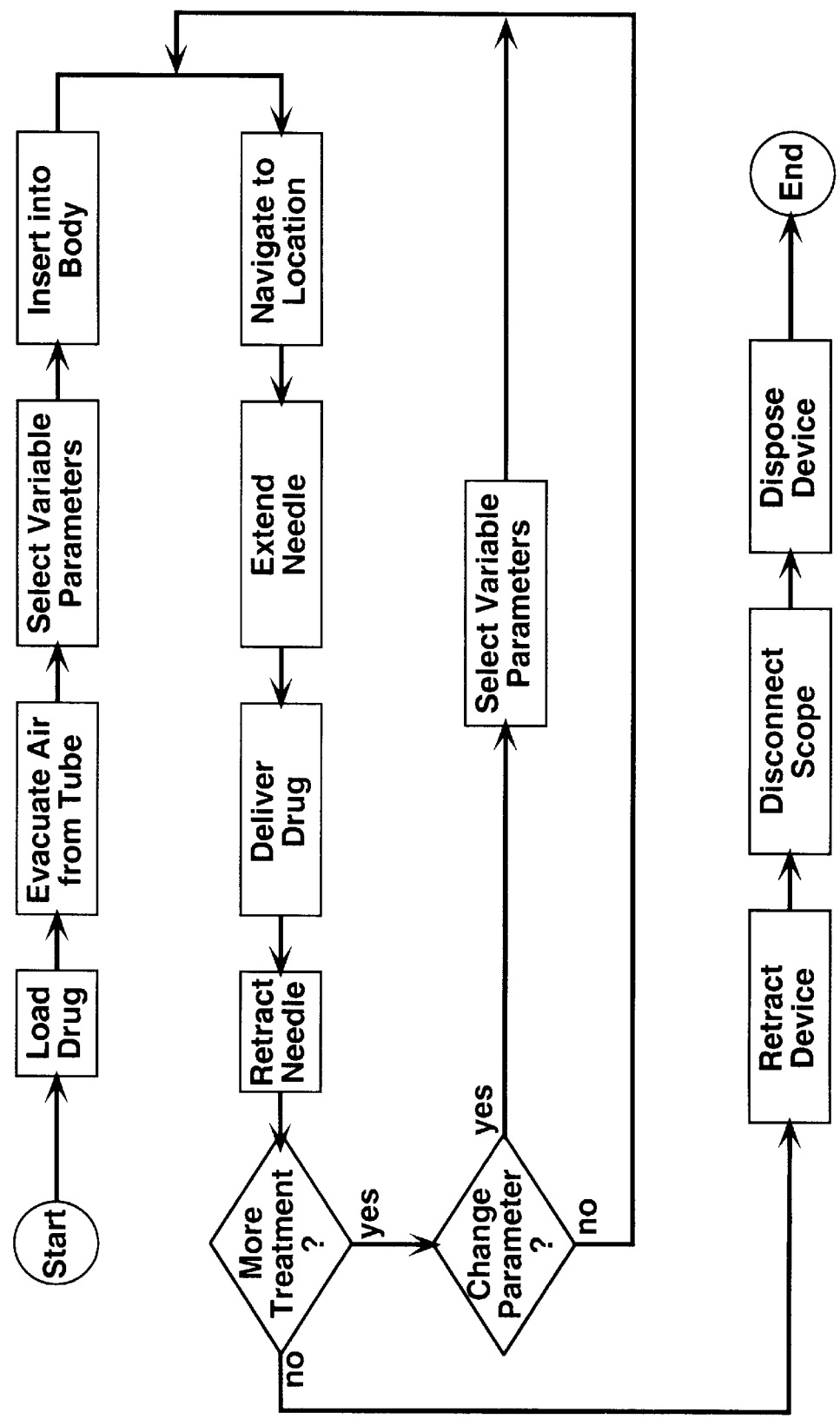
FIG. 7C is a flowchart showing the steps of a preferred method of the present invention.

FIG. 7C is a flowchart showing the steps of a preferred method of the present invention. As described in the foregoing, an initial step 1910 involves selection of the desired drug, compound or other material to be delivered with the methods and apparatus of the present invention, and loading that drug or other material into a suitable reservoir, syringe, cartridge, etc. It will be understood that drug packaging may be a function of the type of drug or the method of delivery required by the drug, i.e., cartridge based packaging for efficient device loading, refrigeratable packaging-type material, dual-compound co-loadable cartridge sets, etc.

In a subsequent step 1912, once a drtig or other compound is loaded into the delivery device of the present invention, air and/or other undesirable fluids, gases, solids, etc. are evacuated from the system, including the delivery device components, drug conduit, piercing needle, etc. In general, depending upon the type of procedure being performed and the types of materials being delivered, evacuation of the system will be required to prevent delivery or introduction undesired gases, fluids, etc.

It will be understood that purging air or other undesirable substances out of the device 10 prior to delivery of drug therethrough at the target region is generally necessary. As described, a reservoir of flushing solution, such as a bag of saline, can be connected to the device 10 through flush connector 116. The reservoir can be pressurized in any number of ways. Once the reservoir is pressurized, valve 118 can be opened to allow flow through the delivery device. (Any optional safety or check valves will need to be cleared prior to this step.) The delivery device can be actuated to cause needle advance, and flow of saline or other flush solution will be observed at the distal tip 702 of the needle 186. Valve 118 can then be closed.

Additionally, it will be understood that purging of either the endoscope portions or the catheter portions may be desirable, and flushing around any visualization tip will increase and enhance the quality of images taken therefrom. Based on the foregoing, it will be apparent to those skilled in the art to incorporate any of various flushing systems, including directing jets of flushing solution against the distal tip 210 or 310 of the device, etc.

Furthermore, priming the device 10 and associated auxiliary equipment with actual drug to be used may, in certain circumstances, be necessary or advantageous. These steps will be understood from the apparatus and procedures described herein. Once the device 10 and associated drug conduits and piercing tips have been purged, priming of the system would include installing the drug syringe or reservoir into the device, switching valve 118 so as to provide communication from the reservoir, through valve 118, through line 128, into the advanceable drug conduit (such as indicated by 282 and 382 herein) and through to the distal, sharpened distal piercing tip 702 of needle 186.

Selection of variable parameters, as shown in step 1914, is necessary. Depending upon the application for the delivery device and associated endoscope or catheter devices, end-user adjustable variable parameters include, but are not limited to, dosage volume, needle advance/retraction speed, needle advance length, dosage rate, etc. In a subsequent step 1916, the interventional end (such as identified as 210 and/or 310) is inserted into the patient's body, e.g., as described with respect to FIG. 7A.

In step 1918, the interventional drug delivery distal end (such as identified as 210 and/or 310) is positioned adjacent target tissue or within a target region. As described, a conventional, endoscope with auxiliary illumination, optionally coupled to a CCD camera for visualization on a real-time monitor, or a catheter device with enhanced visualization capability can be used to navigate the interventional distal drug delivery end to the desired internal location. The delivery device-actuated distal drug delivery piercing needle is extended in step 1920, and as described above, the piercing needle tip can be extended by means of a manually operated trigger-type assembly. Alternatively, a rapidly deployable delivery device, such as described with respect to the preferred embodiment of the present invention, can be used. In the heretofore described manner, drug or other material is delivered to the desired site in step 1922 and the drug delivery piercing needle is thereafter retracted, as shown in step 1924.

The method of the present invention requires that a decision be made, either by the physician, surgeon or cardiologist, an operator or by a programmable or pre-programmed logic controller. In step 1926, if additional treatment, i.e., additional or alternate drug delivery such as to the same or to different sites is desired, then another decision is made with regard to the current parameters previously set such as in step 1914. If the pre-set parameters are sufficient to proceed, i.e. no changes to operator adjustable parameters is required, then steps including navigating the interventional distal drug delivery piercing needle end to the additional desired target tissue or region 1918, extending the needle 1920 as desired, delivery of drug or other compound or material to the desired tissue or region 1922, subsequent retraction of distal piercing needle 1924 and subsequent repetition of the foregoing steps. If, however, the pre-set parameters need to be changed, as determined in step 1928, then the desired parameters are changed in step 1930 and the steps of navigating 1918, extending the needle 1920, delivery of drug or other material 1922, retraction of the needle 1924, and subsequent repetition if and as desired, are repeated.

Once treatment has been completed, such as determined in step 1926, the interventional end and/or other portions of the devices of the present invention are retracted from the patient's body in step 1932, the re-usable endoscope portions or catheter visualization devices are disconnected 1934 and the associated catheter and/or endoscopic portions of the DDM can be disposed of in an ultimate step 1936.

FIG. 8 is a representative schematic drawing of components of a delivery device 10 kit 800 of the present invention. As described above, the present invention is directed to both modular as well as unitary devices. Therefore, the kit 800 comprises the delivery device 10 and associated auxiliary equipment, including endoscope housing mount 206 and elongated tubular portion 208 as well as catheter steering housing 314, elongated tubular shaft portion 308 and associated assembly.

Thus, a single kit 800 will serve the medical practitioner with a wide range of drug delivery options. Drug delivery in surgical procedures, MIS procedures as well as catheter or other percutaneous procedures can be achieved using solely the contents of the delivery device kit 800 of the present invention. According to the present invention, the delivery device 10 provides simple to operate, single squeeze action, manually operated needle advance and drug delivery at some remote target point through an advanceable and controllable drug conduit.

Unless defined otherwise, all technical and scientific terms used herein have the same meaning as commonly understood by one of ordinary skill in the art to which this invention belongs. Although any methods and materials similar or equivalent to those described can be used in the practice or testing of the present invention, the preferred methods and materials are now described.

While the principles of the invention have been made clear in illustrative embodiments, there will be immediately obvious to those skilled in the art many modifications of structure, arrangement, proportions, the elements, materials, and components used in the practice of the invention, and otherwise, which are particularly adapted to specific environments and operative requirements without departing from those principles. The appended claims are intended to cover and embrace any and all such modifications, with the limits only of the true purview, spirit and scope of the invention.

It is claimed:

1. Apparatus for delivery of a drug solution to a target site within a subject by needle injection, comprising
   (a) a delivery device having (i) a housing, (ii) a fluid reservoir, (iii) a carriage assembly mounted in said housing for movement between retracted and extended conditions, and (iv) an actuator assembly operatively connected to said carriage and said reservoir, to cause movement of said carriage from its retracted toward its extended position, and cause flow of fluid from said reservoir, as said actuator is moved from open to closed positions, and
   (b) an appliance maneuverable within a subject to such target site, said appliance having an elongate hollow body probe defining a length having proximal and distal ends, and an inner lumen extending therebetween, an extension member extending substantially said length of said probe from said proximal probe end to said distal probe end, and a needle carried at said distal probe end of said extension member,
   wherein said extension member is operatively connected to said carriage, and said needle is in fluid communication with said reservoir, such that (i) movement of said carriage assembly from its retracted to its extended position is transmitted through said extension member to said needle at said distal probe end, causing said needle to move from a retracted position to an injection position into said target site, and (ii) fluid contained in said reservoir is forced from said reservoir through said needle and delivered into said target site.

2. The apparatus of claim 1, wherein said actuator assembly includes (i) an actuator mounted on said housing for movement between open and closed positions, (ii) advancing means operatively connecting said actuator to said carriage assembly, to advance said carriage assembly toward its extended position when said actuator is moved away from its open position, toward its closed position, and (iii) compressing means operatively connecting said actuator to said reservoir for compressing said reservoir when said actuator is moved from its open position, toward its closed condition.

3. The apparatus of claim 2, wherein said advancing means is effective to advance said carriage assembly toward its extended position when said actuator is moved from its open position, toward a position intermediate its open position and closed position, and said compressing means is effective to compress said reservoir when said actuator is moved from a position intermediate its open position and closed position toward its closed position.

4. The device of claim 2, wherein said reservoir is contained in said housing, and is a syringe barrel having an outlet in fluid communication with said needle, and said compressing means includes a plunger movable within said barrel toward said outlet, to expel fluid from said reservoir.

5. The apparatus of claim 4, wherein said actuator includes a handle operable between said open and closed positions, and a pivoting member mounted in said housing for pivoting movement in forward and reverse directions as said actuator is moved between open and closed positions, respectively, and said compressing means further includes (a) a sliding bar operatively engageable at one bar end with said plunger, (b) a reciprocating bar connected at one bar end to said pivoting member, for movement in forward and reverse directions as said pivoting member is pivoted in forward and reverse directions, respectively, and (c) a releasable locking mechanism operably coupling said sliding bar and reciprocating bar, such that successive actuations of said actuator are effective to advance said sliding bar incrementally in a forward direction effective to expel a defined and incremental quantity of fluid from said reservoir with each such actuation.

6. The apparatus of claim 5, wherein said locking mechanism includes first and second pivot plates, said first plate being operatively connected to said reciprocating bar, and adapted to engage or release said sliding bar, as said reciprocating bar is advanced in a forward or reverse direction, respectively; and said second plate being pivotally mounted adjacent said sliding bar, and adapted to release or engage said sliding bar as said reciprocating bar is advanced in a forward or reverse direction, respectively.

7. The apparatus of claim 2, wherein said actuator includes a manually operable handle operable between said open and closed positions, and a pivoting member mounted in said housing for pivoting movement in forward and reverse directions, as said actuator is moved toward and away from its closed position, respectively, and said advancing means is (i) a sliding surface contact between said pivoting member and said carriage assembly, or (ii) a two-condition spring interposed between said pivoting member and carriage assembly, effective to flip from one condition to another, when a selected spring tension is reached, to move said carriage toward its extended position.

8. The apparatus of claim 2, wherein said carriage assembly includes a carriage and a conduit attached thereto, and in fluid communication with said reservoir, and said extension member is a hollow tube in fluid communication with said conduit, for transmitting fluid pressure from said reservoir to said needle.

9. The apparatus of claim 8, wherein drug solution is contained in said distal end of said tube.

10. The apparatus of claim 8, wherein drug solution is contained in a drug container adjacent said distal end of said appliance, and fluid pressure transmitted from said reservoir through said tube is effective to drive drug solution from said container through said needle.

11. The apparatus of claim 2, wherein said carriage assembly includes a carriage and a linkage attached thereto, and said extension is a wire member operatively connected to said linkage, and said device further includes a fluid-carrying tube for transmitting fluid pressure from said reservoir to said needle.

12. The apparatus of claim 1, wherein said appliance is a catheter assembly, and said probe is a hollow catheter sleeve.

* * * * *